US011639515B2

(12) United States Patent
Zhao et al.

(10) Patent No.: US 11,639,515 B2
(45) Date of Patent: May 2, 2023

(54) GENETICALLY ENGINEERED STRAIN FOR PRODUCING PORCINE MYOGLOBIN AND FOOD-GRADE FERMENTATION AND PURIFICATION THEREOF

(71) Applicants: TAIXING DONGSHENG BIO-TECH CO., LTD, Taixing (CN); Jiangnan University, Wuxi (CN)

(72) Inventors: Xinrui Zhao, Wuxi (CN); Bohan Zhang, Wuxi (CN); Jingwen Zhou, Wuxi (CN); Guocheng Du, Wuxi (CN); Jianghua Li, Wuxi (CN); Jian Chen, Wuxi (CN); Fei Yu, Wuxi (CN); Wei Lu, Taixing (CN); Yuan Qian, Taixing (CN)

(73) Assignees: TAIXING DONGSHENG BIO-TECH CO., LTD, Taixing (CN); JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 17/743,716

(22) Filed: May 13, 2022

(65) Prior Publication Data
US 2022/0267823 A1 Aug. 25, 2022

Related U.S. Application Data

(63) Continuation of application No. PCT/CN2021/126637, filed on Oct. 27, 2021.

(30) Foreign Application Priority Data

May 21, 2021 (CN) .......................... 202110558529.5
May 21, 2021 (CN) .......................... 202110560189.X
May 21, 2021 (CN) .......................... 202110561197.6

(51) Int. Cl.
| | | |
|---|---|---|
| C07K 14/805 | (2006.01) |
| A23L 27/26 | (2016.01) |
| C12N 1/16 | (2006.01) |
| A23J 1/18 | (2006.01) |
| C12N 15/81 | (2006.01) |
| A23J 3/04 | (2006.01) |
| C12P 21/02 | (2006.01) |
| C12N 15/52 | (2006.01) |
| B01D 15/42 | (2006.01) |
| B01D 15/36 | (2006.01) |
| B01D 15/34 | (2006.01) |
| B01D 69/02 | (2006.01) |
| C12R 1/84 | (2006.01) |

(52) U.S. Cl.
CPC .............. *C12P 21/02* (2013.01); *A23J 1/18* (2013.01); *B01D 15/34* (2013.01); *B01D 15/363* (2013.01); *B01D 15/426* (2013.01); *B01D 69/02* (2013.01); *C07K 14/805* (2013.01); *C12N 1/165* (2021.05); *C12N 15/52* (2013.01); *C12N 15/815* (2013.01); *C12Y 302/01001* (2013.01); *C12Y 302/01003* (2013.01); *C12Y 302/01007* (2013.01); *C12Y 302/01017* (2013.01); *C12Y 302/01026* (2013.01); *B01D 2325/20* (2013.01); *C12N 2800/102* (2013.01); *C12R 2001/84* (2021.05)

(58) Field of Classification Search
CPC ...... A23L 13/43; A23L 13/30; C12R 2001/84
See application file for complete search history.

(56) References Cited

U.S. PATENT DOCUMENTS

| | | | | |
|---|---|---|---|---|
| 2004/0018588 | A1* | 1/2004 | Contreras ............ | C12N 15/815 435/254.2 |
| 2022/0095654 | A1* | 3/2022 | Varadan ................ | A23L 13/426 |

FOREIGN PATENT DOCUMENTS

| | | |
|---|---|---|
| CN | 105745332 A | 7/2016 |
| CN | 113150120 A | 7/2021 |
| CN | 113186147 A | 7/2021 |
| CN | 113265346 A | 8/2021 |

OTHER PUBLICATIONS

Qin et al., Applied and Environmental Microbiology, 77(11), 3600-3608, Jun. 2011.*
Guy Dodson et. al., "Apomyoglobin as molecular recoginition surface: expression, reconstitution and crystallization of recombinant porcine myoglobin in *Escherichia coli*" Protein Engineering vol. 2 No. 3 p. 233-237. Sep. 30, 1988.
Lee S. NP_999401.1 Genbank. Apr. 11, 2021.

* cited by examiner

*Primary Examiner* — Maryam Monshipouri
(74) *Attorney, Agent, or Firm* — IPro, PLLC

(57) ABSTRACT

The disclosure discloses a genetically engineered strain for producing porcine myoglobin and fermentation and purification thereof, and belongs to the technical field of genetic engineering. The disclosure realizes efficient secretion and expression of porcine myoglobin by integrating the gene of porcine myoglobin in *P. pastoris*. On this basis, optimization of the medium and culture conditions of recombinant *P. pastoris* can significantly increase the titer of porcine myoglobin, so that the titer can reach 285.42 mg/L under fermenter conditions. In addition, by creatively adding different concentrations of ammonium sulfate to fermentation broth step by step, the purity of myoglobin obtained by final concentration is up to 88.0%, and the purification rate is up to 66.1%. The disclosure realizes efficient expression and high purification of porcine myoglobin from various steps such as synthesis, fermentation and purification of porcine myoglobin, and provides broad prospects for industrial production of porcine myoglobin.

10 Claims, 10 Drawing Sheets
Specification includes a Sequence Listing.

SEQUENCE LISTING

<160> NUMBER OF SEQ ID NOS: 44

<210> SEQ ID NO 1
<211> LENGTH: 465
<212> TYPE: DNA
<213> ORGANISM: Artificial Sequence
<220> FEATURE:
<223> OTHER INFORMATION: Synthetic DNA

<400> SEQUENCE: 1

```
atgggtttgt ctgatggtga atggcaattg gttttaaatg tttggggtaa agttgaagct    60
gatgttgcag gtcatggtca agaagttttg atcagattgt ttaaaggtca tccagaaact   120
ttggaaaagt tcgataagtt taaacatttg aagtctgaag atgaaatgaa ggcttcagaa   180
gatttgaaga acatggtaa cactgttttg acagctttgg gtggtatttt gaaaagaaa    240
ggtcatcatg aagcagaatt gactccatta gctcaatctc atgcaacaaa gcataagatc   300
cctgttaagt atttggaatt catttctgaa gcaatcatcc aagttttaca atcaaaacat   360
cctggtgact tggtgctga tgcacaaggt gctatgtcaa aggcattgga attgtttaga   420
aacgatatgg ctgcaaagta caaggaatta ggttttcaag gttaa                  465
```

<210> SEQ ID NO 2
<211> LENGTH: 71
<212> TYPE: DNA
<213> ORGANISM: Artificial Sequence
<220> FEATURE:
<223> OTHER INFORMATION: Synthetic DNA

<400> SEQUENCE: 2

```
aattcgaaac gatggtcgct tggtggtctt tgtttctgta cggtcttcag gtcgctgcac    60
ctgctttggc t                                                         71
```

<210> SEQ ID NO 3
<211> LENGTH: 65
<212> TYPE: DNA
<213> ORGANISM: Artificial Sequence
<220> FEATURE:
<223> OTHER INFORMATION: Synthetic DNA

<400> SEQUENCE: 3

```
aattcgaaac gatgtctttt agatccttgt tggctttgtc tggtttggtt tgttctggtt    60
tggct                                                                65
```

<210> SEQ ID NO 4
<211> LENGTH: 59
<212> TYPE: DNA
<213> ORGANISM: Artificial Sequence
<220> FEATURE:
<223> OTHER INFORMATION: Synthetic DNA

<400> SEQUENCE: 4

```
aattcgaaac gatgaagtta gcatactcct tgttgcttcc attggcagga gtcagtgct     59
```

<210> SEQ ID NO 5
<211> LENGTH: 68
<212> TYPE: DNA
<213> ORGANISM: Artificial Sequence
<220> FEATURE:
<223> OTHER INFORMATION: Synthetic DNA

<400> SEQUENCE: 5

```
aattcgaaac gatgcttttg caagctttcc ttttcctttt ggctggtttt gcagccaaaa    60
``` tatctgca 68

<210> SEQ ID NO 6
<211> LENGTH: 89
<212> TYPE: DNA
<213> ORGANISM: Artificial Sequence
<220> FEATURE:
<223> OTHER INFORMATION: Synthetic DNA

<400> SEQUENCE: 6
aattcgaaac gatgctgggt aagaacgacc caatgtgtct tgttttggtc ttgttgggat    60
tgactgcttt gttgggtatc tgtcaaggt                                      89

<210> SEQ ID NO 7
<211> LENGTH: 89
<212> TYPE: DNA
<213> ORGANISM: Artificial Sequence
<220> FEATURE:
<223> OTHER INFORMATION: Synthetic DNA

<400> SEQUENCE: 7
aattcgaaac gatgactaag ccaacccaag tattagttag atccgtcagt atattatttt    60
tcatcacatt actacatcta gtcgtagct                                      89

<210> SEQ ID NO 8
<211> LENGTH: 65
<212> TYPE: DNA
<213> ORGANISM: Artificial Sequence
<220> FEATURE:
<223> OTHER INFORMATION: Synthetic DNA

<400> SEQUENCE: 8
aattcgaaac gatgaagtgg gttacctttc tctctttgtt gtttcttttc tcttctgctt    60
actct                                                                65

<210> SEQ ID NO 9
<211> LENGTH: 48
<212> TYPE: DNA
<213> ORGANISM: Artificial Sequence
<220> FEATURE:
<223> OTHER INFORMATION: Synthetic DNA

<400> SEQUENCE: 9
atgaagatct tgtctgcttt gttgttgttg ttcactttgg ctttcgct                 48

<210> SEQ ID NO 10
<211> LENGTH: 75
<212> TYPE: DNA
<213> ORGANISM: Artificial Sequence
<220> FEATURE:
<223> OTHER INFORMATION: Synthetic DNA

<400> SEQUENCE: 10
atgaagttgt tgtctttgac tggtgttgct ggtgttttgg ctacttgtgt tgctgctact    60
ccattggtta agaga                                                     75

<210> SEQ ID NO 11
<211> LENGTH: 66
<212> TYPE: DNA
<213> ORGANISM: Artificial Sequence
<220> FEATURE:
<223> OTHER INFORMATION: Synthetic DNA

<400> SEQUENCE: 11

```
atgaggcagg tttggttctc ttggattgtg ggattgttcc tatgtttttt caacgtgtct    60
tctgct                                                                66
```

<210> SEQ ID NO 12
<211> LENGTH: 476
<212> TYPE: DNA
<213> ORGANISM: Artificial Sequence
<220> FEATURE:
<223> OTHER INFORMATION: Synthetic DNA

<400> SEQUENCE: 12

```
tttttgtaga aatgtcttgg tgtcctcgac caatcaggta gccatccctg aaatacctgg    60
ctccgtggca acaccgaacg acctgctggc aacgttaaat tctccggggt aaaacttaaa   120
tgtggagtaa tagaaccaga aacgtctctt cccttctctc tccttccacc gcccgttacc   180
gtccctagga aattttactc tgctggagag cttcttctac ggccccttg cagcaatgct    240 cttcccagca ttacgttgcg ggtaaaacgg aggtcgtgta cccgacctag cagcccaggg   300
atggaaagtc ccggccgtcg ctggcaataa ctgcgggcgg acgcatgtct tgagattatt   360
ggaaaccacc agaatcgaat ataaaaggcg aacacctttc ccaattttgg tttctcctga   420
cccaaagact ttaaatttaa tttatttgtc cctatttcaa tcaattgaac aactat       476
```

<210> SEQ ID NO 13
<211> LENGTH: 154
<212> TYPE: PRT
<213> ORGANISM: Sus scrofa

<400> SEQUENCE: 13

```
Met Gly Leu Ser Asp Gly Glu Trp Gln Leu Val Leu Asn Val Trp Gly
1               5                   10                  15

Lys Val Glu Ala Asp Val Ala Gly His Gly Gln Glu Val Leu Ile Arg
            20                  25                  30

Leu Phe Lys Gly His Pro Glu Thr Leu Glu Lys Phe Asp Lys Phe Lys
        35                  40                  45

His Leu Lys Ser Glu Asp Glu Met Lys Ala Ser Glu Asp Leu Lys Lys
    50                  55                  60

His Gly Asn Thr Val Leu Thr Ala Leu Gly Gly Ile Leu Lys Lys Lys
65                  70                  75                  80

Gly His His Glu Ala Glu Leu Thr Pro Leu Ala Gln Ser His Ala Thr
                85                  90                  95

Lys His Lys Ile Pro Val Lys Tyr Leu Glu Phe Ile Ser Glu Ala Ile
            100                 105                 110

Ile Gln Val Leu Gln Ser Lys His Pro Gly Asp Phe Gly Ala Asp Ala
        115                 120                 125

Gln Gly Ala Met Ser Lys Ala Leu Glu Leu Phe Arg Asn Asp Met Ala
    130                 135                 140

Ala Lys Tyr Lys Glu Leu Gly Phe Gln Gly
145                 150
```

<210> SEQ ID NO 14
<211> LENGTH: 73
<212> TYPE: DNA
<213> ORGANISM: Artificial Sequence
<220> FEATURE:
<223> OTHER INFORMATION: Synthetic DNA

<400> SEQUENCE: 14

```
gtgggttacc tttatctctt tgttgtttct tttctcttct gcttactcta tgggtttgtc    60
tgatggtgaa tgg                                                       73
```

<210> SEQ ID NO 15
<211> LENGTH: 78
<212> TYPE: DNA
<213> ORGANISM: Artificial Sequence
<220> FEATURE:
<223> OTHER INFORMATION: Synthetic DNA

<400> SEQUENCE: 15

```
tatttgtccc tatttcaatc aattgaacaa ctataattcg aaacgatgaa gtgggttacc    60
tttatctctt tgttgttt                                                  78
```

<210> SEQ ID NO 16
<211> LENGTH: 33
<212> TYPE: DNA
<213> ORGANISM: Artificial Sequence
<220> FEATURE:
<223> OTHER INFORMATION: Synthetic DNA

<400> SEQUENCE: 16

```
atagttgttc aattgattga aatagggaca aat                                 33
```

<210> SEQ ID NO 17
<211> LENGTH: 60
<212> TYPE: DNA
<213> ORGANISM: Artificial Sequence
<220> FEATURE:
<223> OTHER INFORMATION: Synthetic DNA

<400> SEQUENCE: 17

```
tctgctttgt tgttgttgtt cactttggct ttcgctatgg gtttgtctga tggtgaatgg    60
```

<210> SEQ ID NO 18
<211> LENGTH: 74
<212> TYPE: DNA
<213> ORGANISM: Artificial Sequence
<220> FEATURE:
<223> OTHER INFORMATION: Synthetic DNA

<400> SEQUENCE: 18

```
atttcaatca attgaacaac tatttcgaaa cgatgaagat cttgtctgct tgttgttgt    60 tgttcacttt ggct                                                      74
```

<210> SEQ ID NO 19
<211> LENGTH: 32
<212> TYPE: DNA
<213> ORGANISM: Artificial Sequence
<220> FEATURE:
<223> OTHER INFORMATION: Synthetic DNA

<400> SEQUENCE: 19

```
cgtttcgaaa tagttgttca attgattgaa at                                  32
```

<210> SEQ ID NO 20
<211> LENGTH: 78
<212> TYPE: DNA
<213> ORGANISM: Artificial Sequence
<220> FEATURE:
<223> OTHER INFORMATION: Synthetic DNA

<400> SEQUENCE: 20

```
tctcttggat tgtgggattg ttcctatgtt ttttcaacgt gtcttctgct gctccagtca    60
acactacaac agaagatg                                                  78
```

<210> SEQ ID NO 21
<211> LENGTH: 78
<212> TYPE: DNA
<213> ORGANISM: Artificial Sequence
<220> FEATURE:
<223> OTHER INFORMATION: Synthetic DNA

<400> SEQUENCE: 21

```
atttcaatca attgaacaac tatttcgaaa cgatgaggca ggtttggttc tcttggattg    60
tgggattgtt cctatgtt                                                  78
```

<210> SEQ ID NO 22
<211> LENGTH: 32
<212> TYPE: DNA
<213> ORGANISM: Artificial Sequence
<220> FEATURE:
<223> OTHER INFORMATION: Synthetic DNA

<400> SEQUENCE: 22

```
cgtttcgaaa tagttgttca attgattgaa at                                  32
```

<210> SEQ ID NO 23
<211> LENGTH: 76
<212> TYPE: DNA
<213> ORGANISM: Artificial Sequence
<220> FEATURE:
<223> OTHER INFORMATION: Synthetic DNA

<400> SEQUENCE: 23

```
gtcttttaga tccttgttgg ctttgtctgg tttggtttgt tctggtttgg ctatgggttt    60
gtctgatggt gaatgg                                                    76
```

<210> SEQ ID NO 24
<211> LENGTH: 77
<212> TYPE: DNA
<213> ORGANISM: Artificial Sequence
<220> FEATURE:
<223> OTHER INFORMATION: Synthetic DNA

<400> SEQUENCE: 24

```
atttgtccct atttcaatca attgaacaac tataattcga acgatgtct tttagatcct     60 tgttggcttt gtctggt                                                   77
```

<210> SEQ ID NO 25
<211> LENGTH: 33
<212> TYPE: DNA
<213> ORGANISM: Artificial Sequence
<220> FEATURE:
<223> OTHER INFORMATION: Synthetic DNA

<400> SEQUENCE: 25

```
atagttgttc aattgattga aatagggaca aat                                 33
```

<210> SEQ ID NO 26
<211> LENGTH: 69
<212> TYPE: DNA
<213> ORGANISM: Artificial Sequence
<220> FEATURE:
<223> OTHER INFORMATION: Synthetic DNA

<400> SEQUENCE: 26

```
aagttagcat actccttgtt gcttccattg gcaggagtca gtgctatggg tttgtctgat    60
ggtgaatgg                                                            69
```

<210> SEQ ID NO 27
<211> LENGTH: 77
<212> TYPE: DNA
<213> ORGANISM: Artificial Sequence
<220> FEATURE:
<223> OTHER INFORMATION: Synthetic DNA

<400> SEQUENCE: 27

```
atttgtccct atttcaatca attgaacaac tataattcga aacgatgaag ttagcatact    60
ccttgttgct tccattg                                                   77
```

<210> SEQ ID NO 28
<211> LENGTH: 33
<212> TYPE: DNA
<213> ORGANISM: Artificial Sequence
<220> FEATURE:
<223> OTHER INFORMATION: Synthetic DNA

<400> SEQUENCE: 28

```
atagttgttc aattgattga aatagggaca aat                                 33
```

<210> SEQ ID NO 29
<211> LENGTH: 78
<212> TYPE: DNA
<213> ORGANISM: Artificial Sequence
<220> FEATURE:
<223> OTHER INFORMATION: Synthetic DNA

<400> SEQUENCE: 29

```
cttttgcaag ctttcctttt cctttggct ggttttgcag ccaaaatatc tgcaatgggt    60
ttgtctgatg gtgaatgg                                                  78
```

<210> SEQ ID NO 30
<211> LENGTH: 78
<212> TYPE: DNA
<213> ORGANISM: Artificial Sequence
<220> FEATURE:
<223> OTHER INFORMATION: Synthetic DNA

<400> SEQUENCE: 30

```
atttgtccct atttcaatca attgaacaac tataattcga aacgatgctt ttgcaagctt    60
tccttttcct tttggctg                                                  78
```

<210> SEQ ID NO 31
<211> LENGTH: 33
<212> TYPE: DNA
<213> ORGANISM: Artificial Sequence
<220> FEATURE:
<223> OTHER INFORMATION: Synthetic DNA

<400> SEQUENCE: 31

```
atagttgttc aattgattga aatagggaca aat                                 33
```

<210> SEQ ID NO 32
<211> LENGTH: 85
<212> TYPE: DNA
<213> ORGANISM: Artificial Sequence
<220> FEATURE:
<223> OTHER INFORMATION: Synthetic DNA

<400> SEQUENCE: 32
cccaatgtgt cttgttttgg tcttgttggg attgactgct tgttgggta tctgtcaagg    60 tatgggtttg tctgatggtg aatgg                                         85

<210> SEQ ID NO 33
<211> LENGTH: 86
<212> TYPE: DNA
<213> ORGANISM: Artificial Sequence
<220> FEATURE:
<223> OTHER INFORMATION: Synthetic DNA

<400> SEQUENCE: 33
atttgtccct atttcaatca attgaacaac tataattcga aacgatgctg ggtaagaacg    60
acccaatgtg tcttgttttg gtcttg                                        86

<210> SEQ ID NO 34
<211> LENGTH: 33
<212> TYPE: DNA
<213> ORGANISM: Artificial Sequence
<220> FEATURE:
<223> OTHER INFORMATION: Synthetic DNA

<400> SEQUENCE: 34
atagttgttc aattgattga aatagggaca aat                                33

<210> SEQ ID NO 35
<211> LENGTH: 87
<212> TYPE: DNA
<213> ORGANISM: Artificial Sequence
<220> FEATURE:
<223> OTHER INFORMATION: Synthetic DNA

<400> SEQUENCE: 35
caagtattag ttagatccgt cagtatatta ttttcatca cattactaca tctagtcgta    60
gctatgggtt tgtctgatgg tgaatgg                                       87

<210> SEQ ID NO 36
<211> LENGTH: 86
<212> TYPE: DNA
<213> ORGANISM: Artificial Sequence
<220> FEATURE:
<223> OTHER INFORMATION: Synthetic DNA

<400> SEQUENCE: 36
atttgtccct atttcaatca attgaacaac tataattcga aacgatgact aagccaaccc    60
aagtattagt tagatccgtc agtata                                        86

<210> SEQ ID NO 37
<211> LENGTH: 33
<212> TYPE: DNA
<213> ORGANISM: Artificial Sequence
<220> FEATURE:
<223> OTHER INFORMATION: Synthetic DNA

<400> SEQUENCE: 37
atagttgttc aattgattga aatagggaca aat                                33

<210> SEQ ID NO 38
<211> LENGTH: 80
<212> TYPE: DNA
<213> ORGANISM: Artificial Sequence
<220> FEATURE:
<223> OTHER INFORMATION: Synthetic DNA

<400> SEQUENCE: 38
ctggtgttgc tggtgttttg gctacttgtg ttgctgctac tccattggtt aagagaatgg    60
gtttgtctga tggtgaatgg                                                80

<210> SEQ ID NO 39
<211> LENGTH: 80
<212> TYPE: DNA
<213> ORGANISM: Artificial Sequence
<220> FEATURE:
<223> OTHER INFORMATION: Synthetic DNA

<400> SEQUENCE: 39
atttcaatca attgaacaac tatttcgaaa cgatgaagtt gttgtctttg actggtgttg    60
ctggtgtttt ggctacttgt                                                80

<210> SEQ ID NO 40
<211> LENGTH: 32
<212> TYPE: DNA
<213> ORGANISM: Artificial Sequence
<220> FEATURE:
<223> OTHER INFORMATION: Synthetic DNA

<400> SEQUENCE: 40
cgtttcgaaa tagttgttca attgattgaa at                                  32

<210> SEQ ID NO 41
<211> LENGTH: 78
<212> TYPE: DNA
<213> ORGANISM: Artificial Sequence
<220> FEATURE:
<223> OTHER INFORMATION: Synthetic DNA

<400> SEQUENCE: 41
ggtggtcttt gtttctgtac ggtcttcagg tcgctgcacc tgctttggct atgggtttgt    60
ctgatggtga atggcaat                                                  78

<210> SEQ ID NO 42
<211> LENGTH: 80
<212> TYPE: DNA
<213> ORGANISM: Artificial Sequence
<220> FEATURE:
<223> OTHER INFORMATION: Synthetic DNA

<400> SEQUENCE: 42
atttgtccct atttcaatca attgaacaac tataattcga acgatggtc gcttggtggt     60 ctttgtttct gtacggtctt                                                80

<210> SEQ ID NO 43
<211> LENGTH: 33
<212> TYPE: DNA
<213> ORGANISM: Artificial Sequence
<220> FEATURE:
<223> OTHER INFORMATION: Synthetic DNA

<400> SEQUENCE: 43
atagttgttc aattgattga aatagggaca aat                                 33

<210> SEQ ID NO 44
<211> LENGTH: 267
<212> TYPE: DNA
<213> ORGANISM: Artificial Sequence
<220> FEATURE:

<223> OTHER INFORMATION: Synthetic DNA

<400> SEQUENCE: 44

```
atgagatttc cttcaatttt tactgctgtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattg ctgctaaaga agaagggta      240 tctctcgaga aaagagaggc tgaagct                                          267
```

GENETICALLY ENGINEERED STRAIN FOR PRODUCING PORCINE MYOGLOBIN AND FOOD-GRADE FERMENTATION AND PURIFICATION THEREOF

The instant application contains a Sequence Listing in TXT format as a file named "seq.txt", created on Oct. 13, 2022, of 13 kB in size, and which is hereby incorporated by reference in its entirety.

TECHNICAL FIELD

The disclosure relates to a genetically engineered strain for producing porcine myoglobin and food-grade fermentation and purification thereof, and belongs to the technical field of genetic engineering.

BACKGROUND

Myoglobin is a heme-containing globular protein structurally similar to the a subunit of hemoglobin, can store oxygen, and can also be used in iron supplements, disease diagnosis and other fields. Myoglobin is closely related to the color of meat. Different states of myoglobin cause different changes in the color of meat. Myoglobin generally exists in three forms: oxy-myoglobin (oxy-Mb), deoxy-myoglobin (deoxy-Mb) and metmyoglobin (met-Mb), the ratio of the three makes meat appear in different colors. In recent years, with the rise of plant-based meat and cell-based meat products, to simulate the real meat color, myoglobin is added to the plant-based meat and cell-based meat products.

Currently, there are two main ways to produce porcine myoglobin: first, a traditional chemical extraction method, i.e., extraction of porcine myoglobin from heart tissue, which has the problems of high cost, long period, low titer, complex process and many by-products not conducive to separation, and it is difficult to apply to large-scale industrial production; and second, heterologous synthesis of porcine myoglobin using eukaryotic expression system, which has not been reported so far, so it is necessary to carry out research on a food-grade host expression system of porcine myoglobin.

Compared with the traditional chemical method, the microbial synthesis method has many advantages, such as reduction of environmental pollution, stable product quality, relatively simple downstream extraction, and higher possibility to achieve low-cost production. For synthesis of porcine hemoglobin by the microbial method, there are two problems to be solved: first, determination of an appropriate medium for the fermentation of recombinant porcine myoglobin (porcine myoglobin has never been expressed in recombinant *Pichia pastoris* before); and second, determination of a fermentation strategy to increase the titer of porcine myoglobin.

In addition, at present, proteins are usually separated and purified from fermentation broth by affinity chromatography, ion exchange chromatography and gel filtration chromatography, mostly relying on an AKTA protein purification instrument. In most reports, the most commonly used method is His-tag purification in affinity chromatography, in which target protein binds to nickel ions and then is eluted with imidazole for purification. However, a purification tag used for enzyme preparations is not recommended for food processing due to the risk of histidine being converted to histamine, causing allergic reactions in humans. Therefore, food-grade porcine myoglobin cannot be purified using the His-tag.

SUMMARY

The disclosure successfully expresses porcine myoglobin in *Pichia pastoris* by screening promoters and signal peptides, achieves a titer of 46.15 mg/L in a shake flask, and increases the titer of porcine myoglobin by optimizing fermentation conditions.

The fermentation broth involved in the disclosure contains a defoaming agent, and a defoaming agent with relatively high concentration may cause an irreversible dissolution reaction of most ultrafiltration membranes, resulting in that the target protein leaks and cannot be concentrated. Therefore, an ultrafiltration cup is not suitable for concentrating porcine myoglobin. Although salting out can achieve the purpose of concentrating fermentation broth, it is not suitable for treating a large amount of fermentation broth due to certain losses in the process of salting out. In addition, porcine myoglobin is tried to be concentrated using a Vivaflow 200 ultrafiltration membrane module, which can quickly concentrate the fermentation broth and effectively avoid loss of protein. To efficiently purify porcine myoglobin, three food-grade purification methods without affinity tags are tried in the patent, namely salting out-desalting-gel filtration chromatography (AKTA), salting out-desalting-DEAE anion exchange chromatography (AKTA), and ultrafiltration concentration-Q anion exchange chromatography (gravity column). However, an AKTA protein purification instrument has low throughput and low purification efficiency, and thus is not suitable for large-scale industrial production. Use of the gravity column can increase the purification throughput, shorten the purification time, and avoid degradation of porcine myoglobin. The ultrafiltration concentration-Q anion exchange chromatography (gravity column) has the advantages of simple operation, low cost, high purification rate, and the like, and can be used in large-scale industrial production.

A first objective of the disclosure is to provide a genetically engineered strain, which uses *P. pastoris* as a host and expresses porcine myoglobin in the *P. pastoris*, and the NCBI Reference Sequence of the porcine myoglobin is NP 999401.1 (the amino acid sequence is shown in SEQ ID NO.13).

In one implementation, the nucleotide sequence of the gene encoding the porcine myoglobin is shown in SEQ ID NO:1.

In one implementation, the porcine myoglobin gene is expressed by an expression vector containing a GAP promoter or a G1 promoter.

In one implementation, the nucleotide sequence encoding the G1 promoter is shown in SEQ ID NO:12.

In one implementation, a signal peptide of the expression vector is selected from signal peptides of α-factor with the nucleotide sequence shown in SEQ ID NO:44, or α-amalyse with the nucleotide sequence shown in SEQ ID NO:2, or Glucoamylase with the nucleotide sequence shown in SEQ ID NO:3, or Inulinase with the nucleotide sequence shown in SEQ ID NO:4, or Invertase with the nucleotide sequence shown in SEQ ID NO:5, or Lysozyme with the nucleotide sequence shown in SEQ ID NO:6, or Killer protein with the nucleotide sequence shown in SEQ ID NO:7, or Serum albumin with the nucleotide sequence shown in SEQ ID NO:8, or sp23 with the nucleotide sequence shown in SEQ ID NO:9, or nsB with the nucleotide sequence shown in SEQ ID NO:10, or pre-Ost1-alpha factor with the nucleotide sequence shown in SEQ ID NO:11.

In one implementation, *P. pastoris* X33 or *P. pastoris* KM71 is used as the host.

A second objective of the disclosure is to provide a method for producing porcine myoglobin by fermentation. The genetically engineered strain expressing porcine myoglobin is fermented in a hemin-containing system, and the system uses glycerol or glucose as a carbon source.

In one implementation, a medium in the hemin-containing system is a YPD medium, a YPG medium or a BMGY medium.

In one implementation, for fermentation in a shake flask, a seed solution of the genetically engineered strain is cultured to an $OD_{600}$ of 6-10, inoculated into a fermentation system at an inoculation amount of 1-5 mL/100 mL, and fermented at 25-35° C., pH of 4.0-7.0, and 150-300 rpm for at least 60 h.

In one implementation, the fermentation system contains 20-40 mg/L of hemin.

In one implementation, in the fermentation system, the carbon source is 10-20 g/L of glycerol, 10-20 g/L of glucose or 10-20 g/L of sorbitol, and a nitrogen source is 15-25 g/L of tryptone, 15-25 g/L of corn syrup, 15-25 g/L of beef extract, 15-25 g/L of diammonium hydrogen phosphate or 15-25 g/L of ammonium sulfate.

In one implementation, for fermentation in a fermenter, the seed solution of the genetically engineered strain is cultured to an $OD_{600}$ of 8-10, inoculated into the fermentation system at an inoculation amount of 5%-10% of the volume of a reaction system, and fermented at 25-35° C., pH of 4.0-7.0, an aeration rate of 1.0-2.0 VVM, and a DO level controlled at 20%-30% for at least 70 h.

In one implementation, when the DO level is not less than 30%, 50-150 mg/L of hemin is added to the fermentation system.

In one implementation, when the DO level is not less than 30%, glycerol is added to the fermentation system.

In one implementation, the fermenter contains 10-30 g of tryptone, 5-15 g of glycerol, 5-15 g of yeast extract, and $1\times10^{-4}$ to $5\times10^{-4}$ g of biotin.

A third objective of the disclosure is to provide a method for separating and purifying porcine myoglobin from microbial fermentation broth. Porcine myoglobin is separated and purified from the fermentation broth by any of the methods described in (a) to (c) as follows:

(a) salting out-desalting-anion exchange method;
(b) salting out-desalting-gel filtration chromatography; and
(c) concentration-anion exchange method.

The fermentation broth is produced by fermentation with the genetically engineered strain, or obtained by the method.

In one implementation, the porcine myoglobin is concentrated by adding ammonium sulfate.

In one implementation, ammonium sulfate powder is slowly added to the fermentation supernatant and stirred until the concentration of ammonium sulfate reaches a saturation of 50-60%; the mixture is allowed to stand at 1-4° C. for 2 h, and centrifuged at 4° C. at 5000-10000 g for 25-35 min to collect the supernatant; ammonium sulfate powder is added to the supernatant until the concentration of ammonium sulfate reaches 60-70%; the mixture is allowed to stand at 1-4° C. overnight, and centrifuged at 5000-10000 g for 25-35 min to collect the precipitate; and the precipitate is redissolved with 10 mM of Tris-HCl buffer at pH 9.20 to obtain a concentrated solution.

In one implementation, when the salting out-desalting-anion exchange method is used, the obtained concentrated solution is loaded into a desalting column, and equilibrated and eluted with 10-15 mM of Tris-HCl buffer at pH 9.0-10.0, an elution peak before the conductivity changes is collected by detecting the conductivity, and a desalted sample is collected; and the obtained desalted sample is loaded into an anion exchange column, equilibrated with 10-15 mM of Tris-HCl buffer at pH 9.0-10.0, and then subjected to gradient elution with 1-2 M of NaCl buffer, and a second elution peak is collected by detecting UV 280 nm to obtain purified porcine myoglobin.

In one implementation, packing materials of the anion exchange chromatography are DEAE-Sepharose and Q Beads 6FF respectively.

In one implementation, when the salting out-desalting-gel filtration chromatography is used, the obtained concentrated solution is loaded into a desalting column, and equilibrated and eluted with 10-15 mM of Tris-HCl buffer at pH 9.0-10.0, an elution peak before the conductivity changes is collected by detecting the conductivity, and a desalted sample is collected; and the obtained desalted sample is loaded into a gel filtration chromatographic column, equilibrated with 10-15 mM of Tris-HCl buffer at pH 9.0-10.0, and then eluted with 10-15 mM of Tris-HCl buffer at pH 9.0-10.0, and an elution peak is collected by detecting UV 280 nm to obtain purified porcine myoglobin.

In one implementation, a packing material of the gel filtration chromatography is Superdex.

In one implementation, when the concentration-anion exchange method is used, the obtained concentrated solution is further concentrated using a membrane module; the obtained concentrated supernatant is loaded into an anion exchange column, equilibrated with 10-15 mM of Tris-HCl buffer at pH 9.0-10.0, and then subjected to gradient elution with 1-2 M of NaCl buffer, and the eluate with the elution concentration of 20% NaCl is collected, namely pure myoglobin.

In one implementation, the membrane module is: Vivaflow 200 tangential flow filtration membrane module.

In one implementation, a buffer B solution is used for elution, and the salinity of the buffer B is 10%-90%.

In one implementation, myoglobin with the molecular weight greater than 10 kDa is cut off by the membrane module.

In one implementation, a packing material of the desalting column is Sephadex G-25.

In one implementation, a membrane material of the concentration membrane module is polypropylene.

In one implementation, the obtained pure porcine myoglobin may be subjected to heme extraction and optical detection.

A fourth objective of the disclosure is to provide application of the genetically engineered strain in preparation of a product containing myoglobin or a myoglobin derivative.

A fifth objective of the disclosure is to provide a fermentation method for improving porcine myoglobin production by recombinant *P. pastoris*, or application of the method for producing porcine myoglobin in producing porcine myoglobin or a derivative product thereof.

Beneficial Effects:

(1) The disclosure realizes efficient synthesis and production of porcine myoglobin in *P. pastoris*, and solves the problem that porcine myoglobin could not be expressed in a microbial host in the past. By selecting a suitable expression system, porcine myoglobin can be efficiently expressed in *P. pastoris*. At a shake-flask level, the titer of porcine myoglobin is up to 46.15 mg/L, which lays a foundation for application of the porcine myoglobin in artificial meat and other fields of food processing.

(2) By further optimizing the dissolved oxygen conditions and the fed-batch concentration of hemin in the fermentation process, the growth and the ability to secrete and synthesize porcine myoglobin of yeast are enhanced, and porcine myoglobin is efficiently expressed in *P. pastoris* at a fermenter level. At the fermenter level, the titer of porcine myoglobin is up to 285.42 mg/L, which lays a foundation for application of the porcine myoglobin in artificial meat and other fields of food processing.

(3) The fermentation broth of recombinant *P. pastoris* expressing porcine myoglobin is concentrated by creatively adding different concentrations of ammonium sulfate to the fermentation broth, and further concentrated by ultrafiltration, and the concentrated solution is purified, in this way, the purity of the obtained myoglobin is 88.04%, and the purification rate is up to 66.05%, which realizes purification of the porcine myoglobin from the fermentation broth, solves the problem that the fermentation broth of porcine myoglobin is difficult to purify in the past, and realizes efficient purification of the fermentation broth of porcine myoglobin.

DETAILED DESCRIPTION

Figure 1:
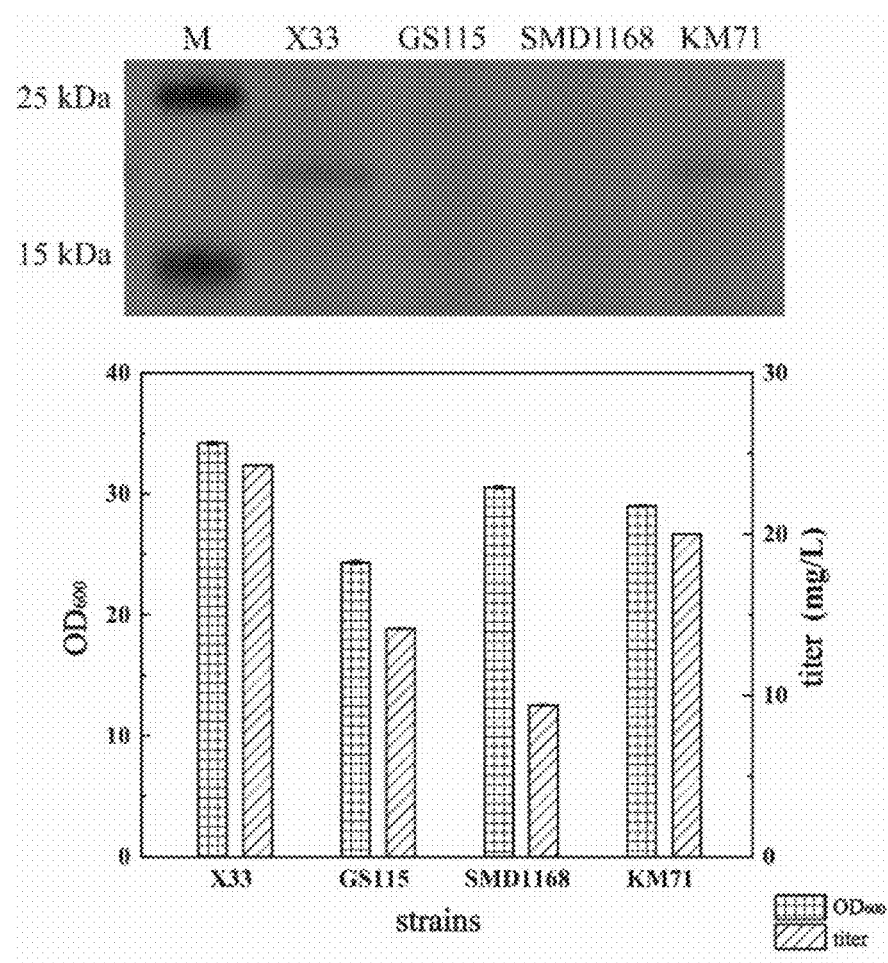
FIG. 1 shows a SDS-PAGE analysis and a titer diagram of porcine myoglobin produced by fermentation of recombinant strains *P. pastoris* X33-α GAP-Mb, *P. pastoris* GS115-α GAP-Mb, *P. pastoris* KM71-α GAP-Mb, and *P. pastoris* SMD1168-α GAP-Mb.

Determination of yeast $OD_{600}$: 1 mL of yeast solution is added into a centrifuge tube, and the corresponding yeast solution is pipetted, diluted with sterile water the corresponding multiple, and measured in a UV spectrophotometer. The step is repeated three times.

Determination of protein content: A Bradford protein concentration assay kit developed by Beyotime Institute of Biotechnology is used for detection. Refer to the instructions for use of the kit for the specific operation steps.

YPD medium: Each liter of YPD medium contains 20 g of tryptone, 20 g of glucose and 10 g of yeast extract; and 20 g of agar powder is added for per liter of solid medium.

YPG medium: Each liter of YPG medium contains 20 g of tryptone, 20 g of glucose and 10 g of glycerol; and 20 g of agar powder is added for per liter of solid medium.

BMGY medium: Each liter of BMGY medium contains 20 g of tryptone, 10 g of glycerol, 10 g of yeast extract, and $4 \times 10^{-4}$ g of biotin.

Composition of the fermentation medium of a fermenter: BMGY medium and hemin with the final concentration of 40 mg/L.

Composition of the fermentation medium in a shake flask: BMGY medium and hemin with the final concentration of 40 mg/L.

Determination of protein content: A Bradford protein concentration assay kit developed by Beyotime Institute of Biotechnology is used for detection. Refer to the instructions for use of the kit for the specific operation steps.

TABLE 1

Primers used in the examples

| Primer | Sequence | |
|---|---|---|
| HSA-F1 | GTGGGTTACCTTTATCTCTTTGTTGTTTCTTTTCTCTTCTGCTTACT CTATGGGTTTGTCTGATGGTGAATGG | SEQ ID NO: 14 |

TABLE 1-continued

Primers used in the examples

| Primer | Sequence | |
|---|---|---|
| HSA-F2 | TATTTGTCCCTATTTCAATCAATTGAACAACTATAATTCGAAACGAT GAAGTGGGTTACCTTTATCTCTTTGTTGTTT | SEQ ID NO: 15 |
| HSA-R | ATAGTTGTTCAATTGATTGAAATAGGGACAAAT | SEQ ID NO: 16 |
| SP23-F1 | TCTGCTTTGTTGTTGTTGTTCACTTTGGCTTTCGCTATGGGTTTGTC TGATGGTGAATGG | SEQ ID NO: 17 |
| SP23-F2 | ATTTCAATCAATTGAACAACTATTTCGAAACGATGAAGATCTTGTCT GCTTTGTTGTTGTTGTTCACTTTGGCT | SEQ ID NO: 18 |
| SP23-R | CGTTTCGAAATAGTTGTTCAATTGATTGAAAT | SEQ ID NO: 19 |
| pre-Ost1-F1 | TCTCTTGGATTGTGGGATTGTTCCTATGTTTTTTCAACGTGTCTTCT GCTGCTCCAGTCAACACTACAACAGAAGATG | SEQ ID NO: 20 |
| pre-Ost1-F2 | ATTTCAATCAATTGAACAACTATTTCGAAACGATGAGGCAGGTTTGG TTCTCTTGGATTGTGGGATTGTTCCTATGTT | SEQ ID NO: 21 |
| pre-Ost1-R | CGTTTCGAAATAGTTGTTCAATTGATTGAAAT | SEQ ID NO: 22 |
| Glu-F1 | GTCTTTTAGATCCTTGTTGGCTTTGTCTGGTTTGGTTTGTTCTGGTT TGGCTATGGGTTTGTCTGATGGTGAATGG | SEQ ID NO: 23 |
| Glu-F2 | ATTTGTCCCTATTTCAATCAATTGAACAACTATAATTCGAAACGATG TCTTTTAGATCCTTGTTGGCTTTGTCTGGT | SEQ ID NO: 24 |
| Glu-R | ATAGTTGTTCAATTGATTGAAATAGGGACAAAT | SEQ ID NO: 25 |
| Inu-F1 | AAGTTAGCATACTCCTTGTTGCTTCCATTGGCAGGAGTCAGTGCTAT GGGTTTGTCTGATGGTGAATGG | SEQ ID NO: 26 |
| Inu-F2 | ATTTGTCCCTATTTCAATCAATTGAACAACTATAATTCGAAACGATG AATTAGCATACTCCTTGTTGCTTCCATTG | SEQ ID NO: 27 |
| Inu-R | ATAGTTGTTCAATTGATTGAAATAGGGACAAAT | SEQ ID NO: 28 |
| Invert-F1 | CTTTTGCAAGCTTTCCTTTTCCTTTTGGCTGGTTTTGCAGCCAAAAT ATCTGCAATGGGTTTGTCTGATGGTGAATGG | SEQ ID NO: 29 |
| Invert-F2 | ATTTGTCCCTATTTCAATCAATTGAACAACTATAATTCGAAACGATG CTTTTGCAAGCTTTCCTTTTCCTTTTGGCTG | SEQ ID NO: 30 |
| Invert-R | ATAGTTGTTCAATTGATTGAAATAGGGACAAAT | SEQ ID NO: 31 |
| Lyso-F1 | CCCAATGTGTCTTGTTTTGGTCTTGTTGGGATTGACTGCTTTGTTGG GTATCTGTCAAGGTATGGGTTTGTCTGATGGTGAATGG | SEQ ID NO: 32 |
| Lyso-F2 | ATTTGTCCCTATTTCAATCAATTGAACAACTATAATTCGAAACGATG CTGGGTAAGAACGACCCAATGTGTCTTGTTTTGGTCTTG | SEQ ID NO: 33 |
| Lyso-R | ATAGTTGTTCAATTGATTGAAATAGGGACAAAT | SEQ ID NO: 34 |
| Killer-F1 | CAAGTATTAGTTAGATCCGTCAGTATATTATTTTTCATCACATTACT ACATCTAGTCGTAGCTATGGGTTTGTCTGATGGTGAATGG | SEQ ID NO: 35 |
| Killer-F2 | ATTTGTCCCTATTTCAATCAATTGAACAACTATAATTCGAAACGATG ACTAAGCCAACCCAAGTATTAGTTAGATCCGTCAGTATA | SEQ ID NO: 36 |
| Killer-R | ATAGTTGTTCAATTGATTGAAATAGGGACAAAT | SEQ ID NO: 37 |
| nsB-F1 | CTGGTGTTGCTGGTGTTTTGGCTACTTGTGTTGCTGCTACTCCATTG GTTAAGAGAATGGGTTTGTCTGATGGTGAATGG | SEQ ID NO: 38 |
| nsB-F2 | ATTTCAATCAATTGAACAACTATTTCGAAACGATGAAGTTGTTGGTC TTTGACTGGTGTTGCTGGTGTTTTGGCTACTTGT | SEQ ID NO: 39 |
| nsB-R | CGTTTCGAAATAGTTGTTCAATTGATTGAAAT | SEQ ID NO: 40 |
| α-amalyse-F1 | GGTGGTCTTTGTTTCTGTACGGTCTTCAGGTCGCTGCACCTGCTTTG GCTATGGGTTTGTCTGATGGTGAATGGCAAT | SEQ ID NO: 41 |

TABLE 1-continued

Primers used in the examples

| Primer | Sequence | |
|---|---|---|
| α-amalyse-F2 | ATTTGTCCCTATTTCAATCAATTGAACAACTATAATTCGAAACGATGGTCGCTTGGTGGTCTTTGTTTCTGTACGGTCTT | SEQ ID NO: 42 |
| α-amalyse-R | ATAGTTGTTCAATTGATTGAAATAGGGACAAAT | SEQ ID NO: 43 |

Example 1: Construction of Recombinant Porcine Myoglobin-Expressing *Pichia pastoris* and Expression of Protein The porcine myoglobin gene (with the nucleotide sequence shown in SEQ ID NO:1) was ligated to a multiple cloning site of an integrated expression vector pGAPZα A to construct a recombinant plasmid pGAPZα A-Mb.

The constructed recombinant plasmid pGAPZα A-Mb was transformed into *Escherichia coli* DH5α to obtain a transformation solution. The transformation solution was spread on an LB plate containing 20 µg/mL Zeocin, and cultured at 37° C. until single colonies grew. The single colonies were picked and verified by PCR and sequencing, and plasmids were extracted from positive colonies verified correct. The extracted plasmids were transformed into *P. pastoris* X33, *P. pastoris* GS115, *P. pastoris* KM71 and *P. pastoris* SMD1168 by electroporation to construct recombinant strains *P. pastoris* X33-α GAP-Mb, *P. pastoris* GS115-α GAP-Mb, *P. pastoris* KM71-α GAP-Mb, and *P. pastoris* SMD1168-α GAP-Mb respectively.

The constructed recombinant *P. pastoris* strains were fermented to produce proteins respectively: a *P. pastoris* seed solution with an $OD_{600}$ of 6-8 was inoculated into 48 mL of YPD medium containing hemin with the final concentration of 20 mg/L at an inoculation amount of 2% (2 mL/100 mL), and fermented at 30° C., 220 rpm for at least 60 h. The expression of porcine myoglobin in the fermentation supernatant was detected by SDS-PAGE and the Bradford protein concentration assay kit.

As shown in FIG. 1, the recombinant strains *P. pastoris* X33-α GAP-Mb (with a titer of 24.25 mg/L) and *P. pastoris* KM71-α GAP-Mb (with a titer of 20.01 mg/L) could express porcine hemoglobin, while *P. pastoris* GS115-α GAP-Mb and *P. pastoris* SMD1168-α GAP-Mb could not express porcine myoglobin. Lanes 1 to 4 corresponded to *P. pastoris* X33-α GAP-Mb, *P. pastoris* GS115-α GAP-Mb, *P. pastoris* SMD1168-α GAP-Mb, and *P. pastoris* KM71-α GAP-Mb respectively.

Example 2: Transformation of Recombinant Porcine Myoglobin-Expressing *P. pastoris* and Expression of Protein (1) Transformation of Signal Peptides Signal peptides α-amalyse (with the nucleotide sequence shown in SEQ ID NO:2), Glucoamylase (with the nucleotide sequence shown in SEQ ID NO:3), Inulinase (with the nucleotide sequence shown in SEQ ID NO:4), Invertase (with the nucleotide sequence shown in SEQ ID NO:5), Lysozyme (with the nucleotide sequence shown in SEQ ID NO:6), Killer protein (with the nucleotide sequence shown in SEQ ID NO:7), Serum albumin-HSA (with the nucleotide sequence shown in SEQ ID NO:8), sp23 (with the nucleotide sequence shown in SEQ ID NO:9), nsB (with the nucleotide sequence shown in SEQ ID NO:10) and pre-Ost1-alpha factor (with the nucleotide sequence shown in SEQ ID NO:11) were synthesized, and inserted into plasmids pGAPZα A-Mb respectively to replace original α-factor signal sequences.

① Construction of a pGAPZα A-α-amalyse GAP-Mb plasmid: a pGAPZαA-Mb plasmid was used as a template, and primary amplification was performed using primers α-amalyse-F1 and α-amalyse-R to obtain a primary PCR product; and then the primary PCR product was used as a template, secondary amplification was performed using primers α-amalyse-F2 and α-amalyse-R, and the PCR product was recovered. The correct pGAPZαA-α-amalyse-Mb plasmid was obtained by DNA sequencing and verification.

② Construction of a pGAPZα A-Glucoamalyse GAP-Mb plasmid: specific construction steps are as described in the aforementioned plasmid construction method. Primers Glu-F1 and Glu-R were used for performing primary PCR; primers Glu-F2 and Glu-R were used for performing secondary PCR; and the plasmid was constructed.

③ Construction of a pGAPZα A-Inu GAP-Mb plasmid: specific construction steps are as described in the aforementioned plasmid construction method. Primers Inu-F1 and Inu-R were used for performing primary PCR; primers Inu-F2 and Inu-R were used for performing secondary PCR; and the plasmid was constructed.

④ Construction of a pGAPZα A-Invertase GAP-Mb plasmid: specific construction steps are as described in the aforementioned plasmid construction method. Primers Invert-F1 and Invert-R were used for performing primary PCR; primers Invert-F2 and Invert-R were used for performing secondary PCR; and the plasmid was constructed.

⑤ Construction of a pGAPZAα A-Lysoenzyme GAP-Mb plasmid: specific construction steps are as described in the aforementioned plasmid construction method. Primers Lyso-F1 and Lyso-R were used for performing primary PCR; primers Lyso-F2 and Lys-R were used for performing secondary PCR; and the plasmid was constructed.

⑥ Construction of a pGAPZα A-Killer protein GAP-Mb plasmid: specific construction steps are as described in the aforementioned plasmid construction method. Primers Killer protein-F1 and Killer protein-R were used for performing primary PCR; primers Killer protein-F2 and Killer protein-R were used for performing secondary PCR; and the plasmid was constructed.

⑦ Construction of a pGAPZα A-HSA GAP-Mb plasmid: specific construction steps are as described in the aforementioned plasmid construction method. Primers HSA-F1 and HSA-R were used for performing primary PCR; primers HSA-F2 and HSA-R were used for performing secondary PCR; and the plasmid was constructed.

⑧ Construction of a pGAPZα A-sp23 GAP-Mb plasmid: specific construction steps are as described in the aforementioned plasmid construction method. Primers sp23-F1 and sp23-R were used for performing primary PCR; primers sp23-F2 and sp23-R were used for performing secondary PCR; and the plasmid was constructed.

⑨ Construction of a pGAPZα A-nsB GAP-Mb plasmid: specific construction steps are as described in the aforementioned plasmid construction method. Primers nsB-F1 and nsB-R were used for performing primary PCR; primers nsB-F2 and nsB-R were used for performing secondary PCR; and the plasmid was constructed.

⑩ Construction of a pGAPZα A-pre-Ost1 GAP-Mb plasmid: specific construction steps are as described in the aforementioned plasmid construction method. Primers pre-Ost1-F1 and pre-Ost1-R were used for performing primary PCR; primers pre-Ost1-F2 and pre-Ost1-R were used for performing secondary PCR; and the plasmid was constructed.

The constructed recombinant plasmids pGAPZα A-α-amalyse GAP-Mb, pGAPZα A-Glucoamylase GAP-Mb, pGAPZα A-Inulinase GAP-Mb, pGAPZα A-Invertase GAP-Mb, pGAPZα A-Lysozyme GAP-Mb, pGAPZα A-Killer protein GAP-Mb, pGAPZα A-HSA GAP-Mb, pGAPZα A-sp23 GAP-Mb, pGAPZα A-nsB GAP-Mb, and pGAPZα A-pre-Ost1 GAP-Mb were transformed into *E. coli* DH5α respectively. The transformation solution was spread on an LB plate containing Zeocin, and cultured at 37° C. until single colonies grew. The single colonies were verified by PCR and sequencing, and plasmids were extracted from correct positive single colonies. The extracted plasmids were transformed into *P. pastoris* X33 strains by electroporation, to construct recombinant strains *P. pastoris* X33-α-amalyse GAP-Mb, *P. pastoris* X33-Glucoamylase GAP-Mb, *P. pastoris* X33-Inulinase GAP-Mb, *P. pastoris* X33-Invertase GAP-Mb, *P. pastoris* X33-Killer protein GAP-Mb, *P. pastoris* X33-HSA GAP-Mb, *P. pastoris* X33-sp23 GAP-Mb, *P. pastoris* X33-nsB GAP-Mb, and *P. pastoris* X33-pre-Ost1 GAP-Mb respectively.

The constructed recombinant *P. pastoris* strains were fermented to produce proteins respectively: a *P. pastoris* seed solution with an $OD_{600}$ of 6-8 was inoculated into 48 mL of YPD medium containing 20 mg/L of hemin at an inoculation amount of 2% (2 mL/100 mL), and fermented at 30° C., 220 rpm for at least 60 h. The expression of porcine myoglobin in the fermentation supernatant was detected by SDS-PAGE and the Bradford protein concentration assay kit.

Figure 2:
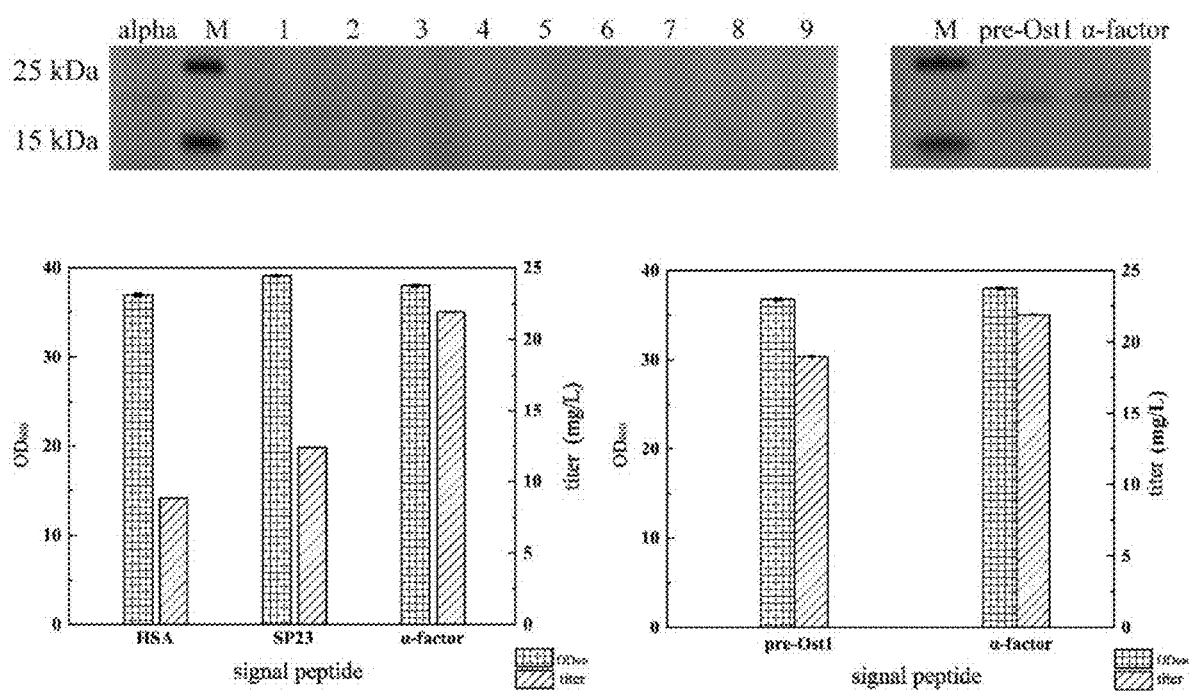
FIG. 2 shows a SDS-PAGE analysis and a titer diagram of porcine myoglobin produced by fermentation of recombinant strains with different signal peptides, and lanes 1 to 9 represent *P. pastoris* X33-SP23-Mb, X33-HSA-Mb, X33-α-amylase-Mb, X33-nsB-Mb, X33-Inulinase-Mb, X33-Invertase-Mb, X33-Glucoamylase-Mb, X33-Killer protein-Mb and X33-Lysozyme-Mb respectively.

The results are shown in FIG. 2. Lanes 1 to 9 represent *P. pastoris* X33-SP23 GAP-Mb, X33-HSA GAP-Mb, X33-α-amylase GAP-Mb, X33-nsB GAP-Mb, X33-Inulinase GAP-Mb, X33-Invertase GAP-Mb, X33-Glucoamylase GAP-Mb, X33-Killer protein GAP-Mb, and X33-Lysozyme GAP-Mb respectively. Lanes in the gel diagram on the right represent *P. pastoris* X33-pre-Ost1-Mb, and X33-HSA GAP-Mb respectively.

It can be seen from FIG. 2 that *P. pastoris* X33-α GAP-Mb, X33-SP23 GAP-Mb, X33-HSA GAP-Mb, and X33-pre-Ost1-Mb can secrete porcine myoglobin, with the titers of 21.90, 12.38, 8.84, and 19.01 mg/L respectively.

(2) Transformation of Promoters

A G1 promoter sequence (with the nucleotide sequence shown in SEQ ID NO:12) was synthesized. The plasmid pGAPZα-A-Mb was used as a template, and a GAP promoter was replaced with a G1 promoter by means of restriction enzyme ligation to obtain a recombinant plasmid pG1-Mb.

The recombinant plasmid pG1-Mb was transformed into *E. coli* DH5a. The transformation solution was spread on an LB plate containing Zeocin, and cultured at 37° C. until single clones grew. After the single clones were verified by colony PCR and sequencing, plasmids were extracted from correct positive clones. The extracted plasmids were transformed into a *P. pastoris* X-33 strain by electroporation to construct a recombinant strain *P. pastoris* X33-G1-Mb.

Figure 3:
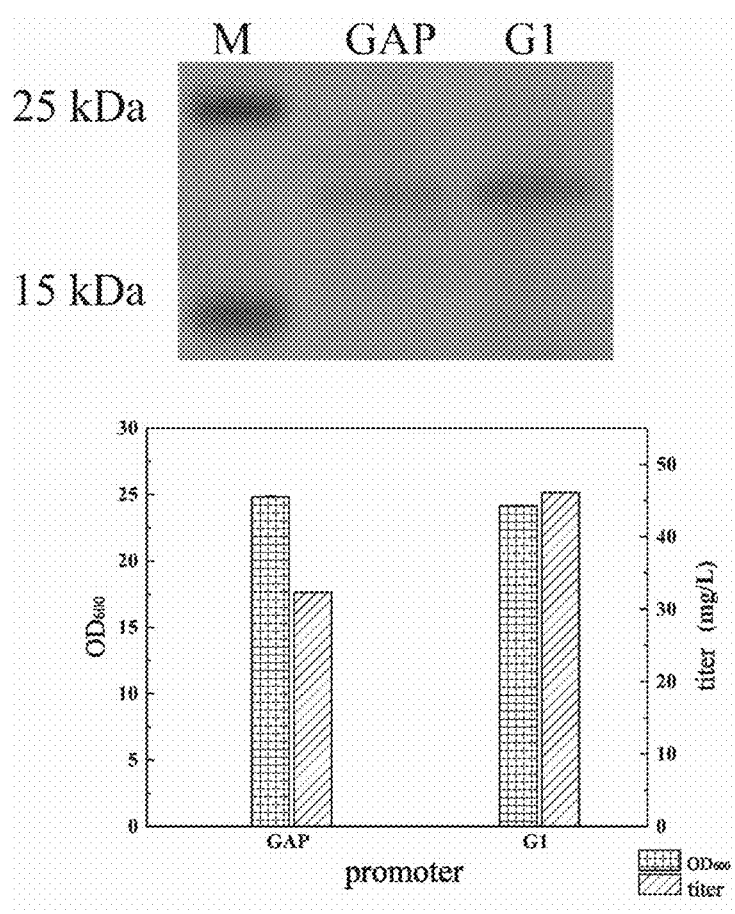
FIG. 3 is a comparative SDS-PAGE analysis and a titer diagram of porcine myoglobin produced by fermentation of recombinant strains *P. pastoris* X33-G1-Mb and *P. pastoris* X33-α GAP-Mb containing G1 promoters.

The constructed recombinant strain *P. pastoris* X33-G1-Mb was fermented to produce proteins: a seed solution with an $OD_{600}$ of 6-8 was inoculated into 48 mL of YPD medium containing hemin with the final concentration of 20 mg/L at an inoculation amount of 2% (2 mL/100 mL), and fermented at 30° C., 220 rpm for at least 60 h. The expression of porcine myoglobin in the fermentation supernatant was detected by SDS-PAGE and the Bradford protein concentration assay kit. The results are shown in FIG. 3. The recombinant strain constructed using the G1 promoter could express porcine myoglobin, and the protein titer was increased to 46.15 mg/L compared with the titer of 21.90 mg/mL of the recombinant strain containing the GAP promoter.

Example 3: Optimization of Fermentation Medium and Fermentation Conditions at Shake Flask Level 1. Preparation of a primary seed solution: the strain *P. pastoris* X33-α GAP-Mb constructed in Example 1 and stored at −80° C. was streaked on a plate. Single colonies were picked and inoculated in a 50 mL sterile culture tube containing 5 mL of YPD medium, and cultured at 30° C., 220 rpm on a shaker for 16-18 h to obtain the primary seed solution.

2. Preparation of a secondary seed solution: the primary seed solution was inoculated into a 250 mL shake flask containing 50 mL of YPD medium at an inoculation amount of 1% (1 mL/100 mL), and cultured at 30° C., 220 rpm on a shaker for 22 h to an $OD_{600}$ of 8-10.

3. Fermentation Conditions:

(1) Production of porcine myoglobin by fermentation of genetically engineered strain in different media The secondary seed solution was inoculated into 250 mL shake flasks containing 49 mL of fermentation medium (YPG, BMGY, and YPD media respectively) at an inoculation amount of 2% (2 mL/100 mL), and fermented at 30° C., 220 rpm for at least 60 h. The fermentation media contained 10 g/L of glycerol and hemin with the final concentration of 20 mg/L.

Figure 4A:
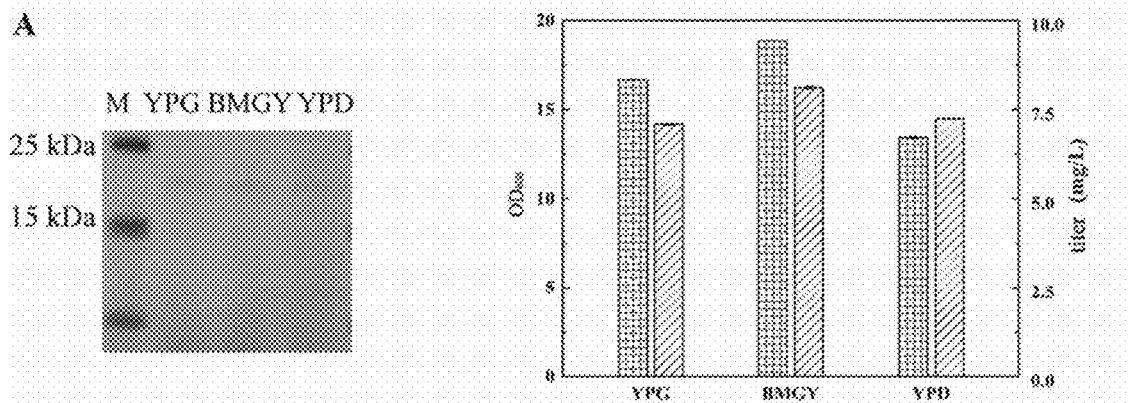
FIG. 4A shows a titer diagram of porcine myoglobin corresponding to different fermentation media at the shake flask level.

The results are shown in FIG. 4A. The titer of porcine myoglobin was the highest when the recombinant strain was cultured in the BMGY medium.

(2) Production of porcine myoglobin by fermentation of genetically engineered strain with different carbon sources The secondary seed solution was inoculated into 250 mL shake flasks containing 49 mL of fermentation medium (each liter of the medium contained 20 g of tryptone, 10 g of yeast extract, $4 \times 10^{-4}$ g of biotin, and hemin with the final concentration of 20 mg/L) at an inoculation amount of 2% (2 mL/100 mL), and fermented for at least 60 h. 10 g/L of glycerol, 10 g/L of glucose, and 10 g/L of sorbitol were additionally added to the fermentation medium respectively.

Figure 4B:
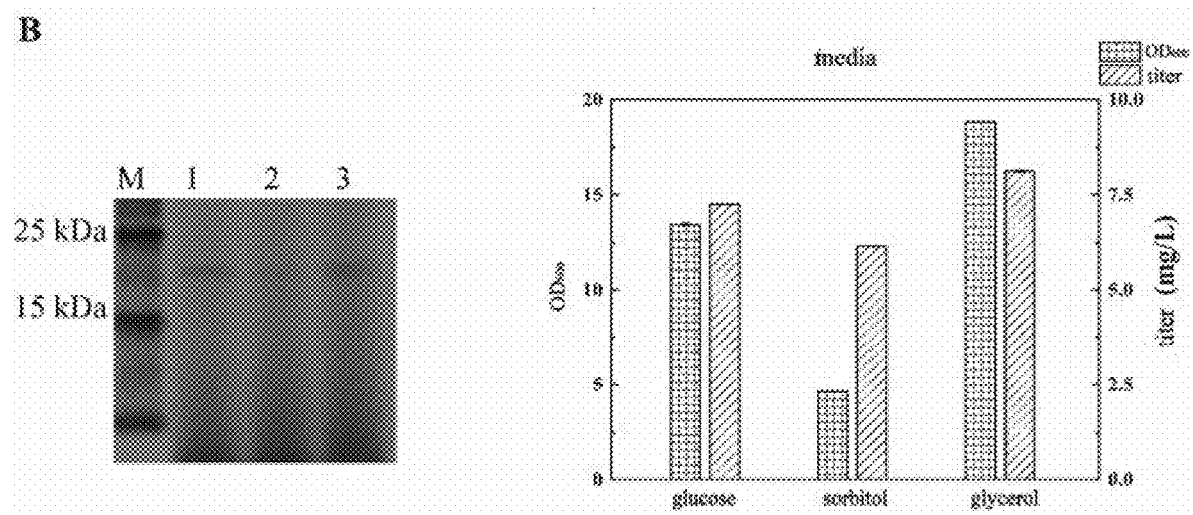
FIG. 4B shows a titer diagram of porcine myoglobin corresponding to different carbon sources at the shake flask level, and lanes 1 to 3 represent glucose, sorbitol and glycerol respectively.

The results are shown in FIG. 4B. The titer of porcine myoglobin was the highest when the carbon source was glycerol.

(3) Production of porcine myoglobin by fermentation of genetically engineered strain with different nitrogen sources The secondary seed solution was inoculated into 250 mL shake flasks containing 49 mL of fermentation medium (each liter of the medium contained 10 g of glycerol, 10 g of yeast extract, $4 \times 10^{-4}$ g of biotin, and hemin with the final concentration of 20 mg/L) at an inoculation amount of 2% (2 mL/100 mL), and fermented for at least 60 h. 20 g/L of tryptone, 20 g/L of corn syrup, 20 g/L of beef extract, 20 g/L of diammonium hydrogen phosphate, and 20 g/L of ammonium sulfate were additionally added to the fermentation medium respectively.

Figure 4C:
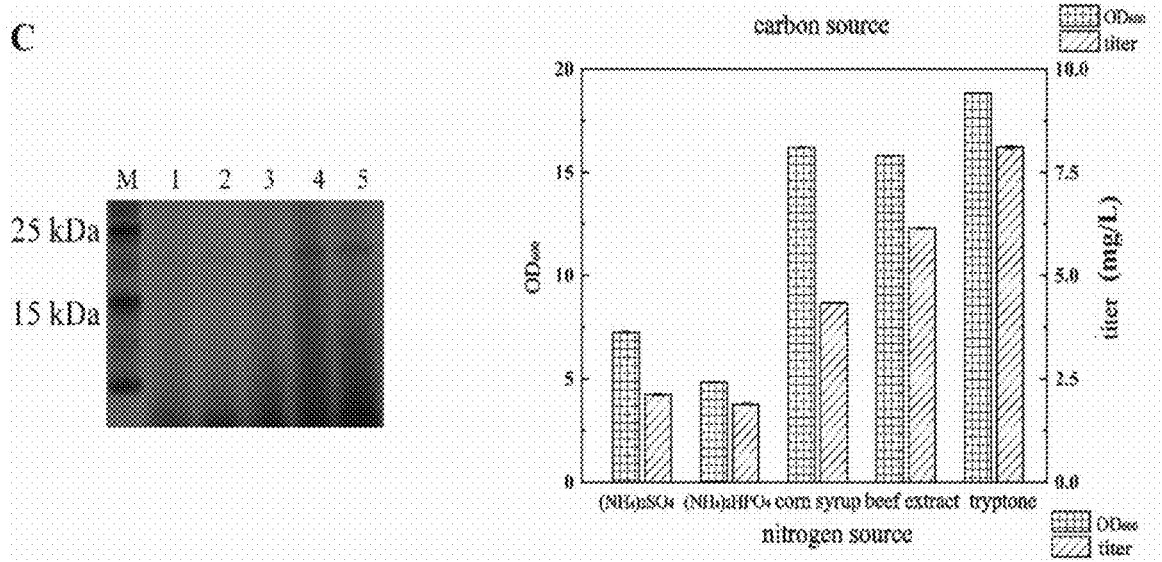
FIG. 4C shows a titer diagram of porcine myoglobin corresponding to different nitrogen sources at the shake flask level, and lanes 1 to 5 represent ammonium sulfate, diammonium hydrogen phosphate, corn syrup, beef extract and tryptone respectively.

The results are shown in FIG. 4C. The titer of porcine myoglobin was the highest when the nitrogen source was tryptone.

(4) Production of porcine myoglobin by fermentation of genetically engineered strain at different temperature The secondary seed solution was inoculated into a 250 mL shake flask containing 49 mL of fermentation medium (the fermentation medium was BMGY) at an inoculation amount of 2%, and fermented for at least 60 h. The fermentation medium contained 10 g/L glycerol and hemin with the final concentration of 20 mg/L.

Figure 5A:
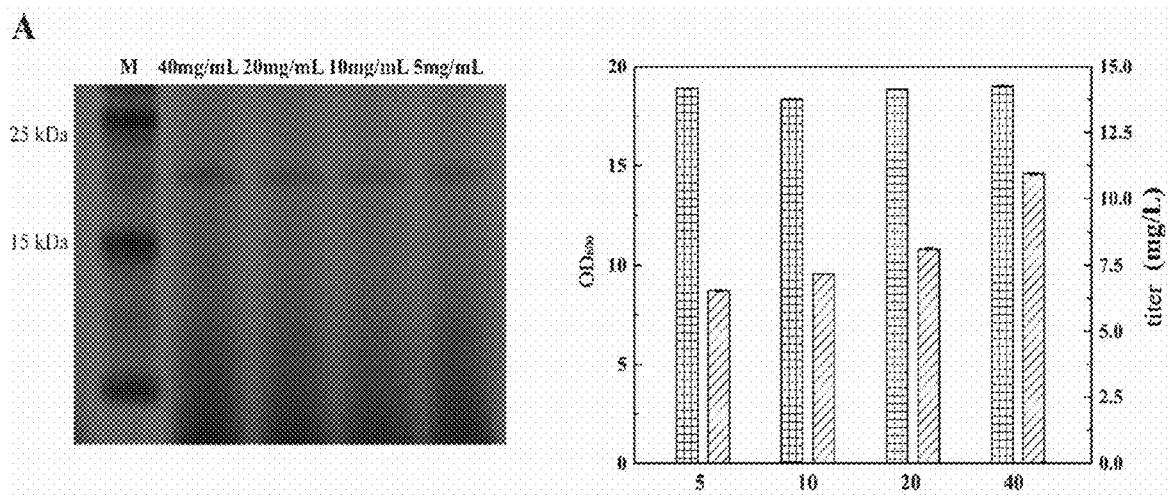
FIG. 5A shows a titer diagram of porcine myoglobin produced by fermentation under different hemin addition concentration at the shake flask level.
Figure 5B:
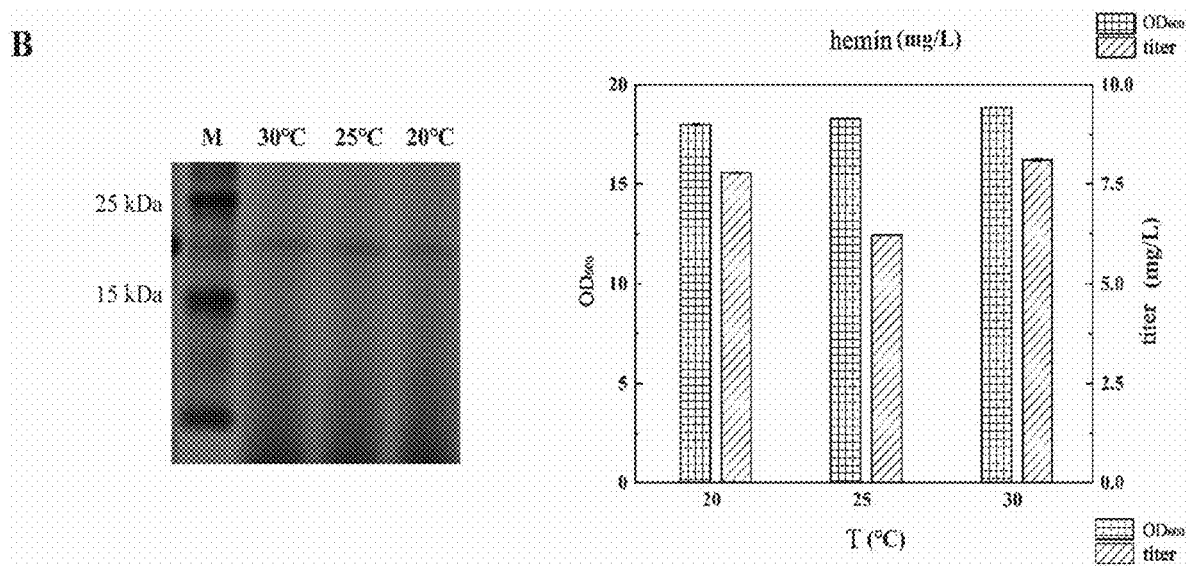
FIG. 5B shows a titer diagram of porcine myoglobin produced by fermentation under different temperature at the shake flask level.

The results are shown in FIG. 5B. Protein expression was the highest when the yeast were fermented at 30° C.

(5) Production of porcine myoglobin by fermentation of genetically engineered strain at different hemin levels The secondary seed solution was inoculated into a 250 mL shake flask containing 49 mL of fermentation medium (the fermentation medium was BMGY) at an inoculation amount of 2% (2 mL/100 mL), and fermented for at least 60 h. The fermentation medium contained hemin with the final concentration of 5, 10, 20, and 40 mg/L respectively. The results are shown in FIG. 5A. When the final concentration of hemin in the medium was 40 mg/L, the titer of porcine myoglobin was higher than those under other conditions.

Example 4: Production of Porcine Myoglobin Under Different Dissolved Oxygen Conditions (Fermenter Level)

1. Preparation of a primary seed solution: the strain *P. pastoris* X33-α GAP-Mb constructed in Example 1 and stored at −80° C. was streaked on a plate. Single colonies were picked and inoculated in a 50 mL sterile culture tube containing 5 mL of YPD medium, and cultured at 30° C., 220 rpm on a shaker for 16-18 h to obtain the primary seed solution.

2. Preparation of a secondary seed solution: the primary seed solution was inoculated into a 250 mL shake flask containing 50 mL of YPD medium at an inoculation amount of 1% (1 mL/100 mL), and cultured at 30° C., 220 rpm on a shaker for 22 h to an $OD_{600}$ of 8-10.

3. Fermentation conditions: the secondary seed solution was inoculated into 5 L fermenters containing 1.8 L of fermentation medium (the fermentation medium was BMGY) at an inoculation amount of 10% (10 mL/100 mL). The fermentation medium contained 10 g/L of glycerol and hemin with the final concentration of 20 mg/L. The pH was controlled at about 5.50. The fermentation of porcine myoglobin was controlled at DO levels of 20%-Stat, 30%-Stat and 40%-Stat respectively, and the fermentation was performed at 30° C., 200-800 rpm and 1.5 VVM for 84 h.

Figure 6:
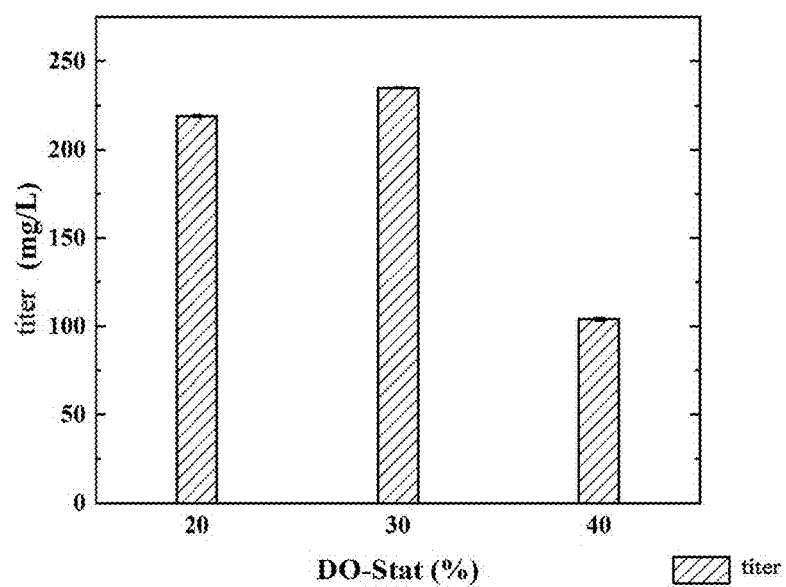
FIG. 6 shows results of optimization of dissolved oxygen at the fermenter level.

The detection results of the porcine myoglobin titer are shown in FIG. 6. When the DO level was controlled at 20%, 30%, and 40%, the titers were 219.13, 235.70, and 103.94 mg/L respectively.

Example 5: Production of Porcine Myoglobin with Different Concentration of Hemin by Fed-Batch (1) Production of porcine myoglobin by fermentation of *P. pastoris* X33-α GAP-Mb
1. Preparation of primary seed solutions: the strains *P. pastoris* X33-α GAP-Mb and *P. pastoris* X33-α G1-Mb constructed in Example 1 and stored at −80° C. were streaked on plates. Single colonies were picked and inoculated in 50 mL sterile culture tubes containing 5 mL of YPD medium, and cultured at 30° C., 220 rpm on a shaker for 16-18 h to obtain the primary seed solutions.

2. Preparation of secondary seed solutions: the primary seed solutions were inoculated into 250 mL shake flasks containing 50 mL of YPD medium at an inoculation amount of 1%, and cultured at 30° C., 220 rpm on a shaker for 22 h to an $OD_{600}$ of 8-10.

3. Fermentation conditions: the seed solutions were inoculated into 5 L fermenters containing 1.8 L of fermentation medium at an inoculation amount of 10%. The fermentation medium contained 10 g/L of glycerol and hemin with the final concentration of 20 mg/L. Fermentation was performed according to a 30% DO-Stat fermentation strategy at an aeration rate of 1.5 VVM and a stirring speed of 200-800 rpm. After about 12 h of fermentation, the glycerol was exhausted and fed at this time. The speed of feeding was mainly automatically controlled by DO and stirring. When DO>30%, 50% (W/V) glycerol was fed, and the feeding amount of glycerol just met the needs of yeast growth. When DO<30%, the stirring speed was increased (the initial speed was 200 rpm, and the maximum speed was 800 rpm). In the process of fed-batch, hemin with the final concentration of 50 mg/L, 100 mg/L, 150 mg/L and 200 mg/L was added together with the glycerol, and fermentation was performed for 84 h.

Figure 7:
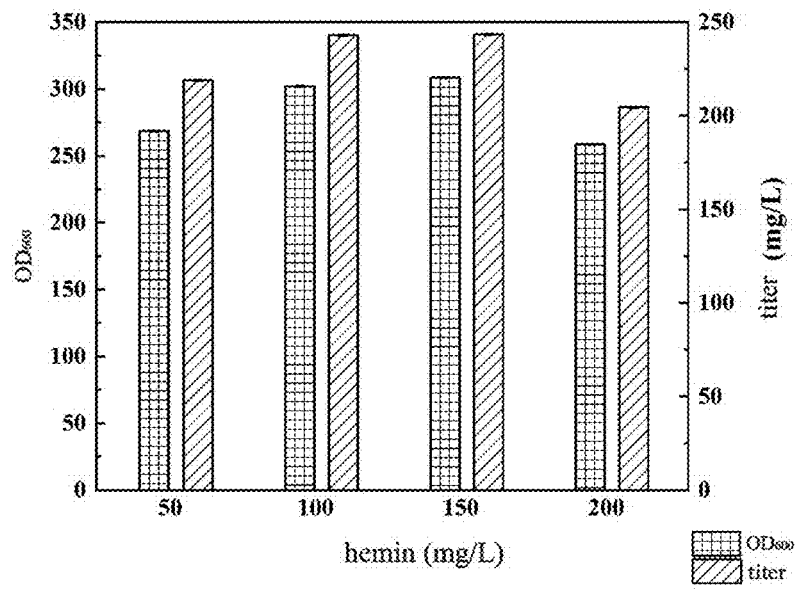
FIG. 7 shows results of optimization of the hemin fed-batch concentration at the fermenter level.

The detection results of the porcine myoglobin titer are shown in FIG. 7. When the final concentration of hemin was 150 mg/L, the titer was the highest, which was 243.43 mg/L. When the final concentration of hemin was 50 mg/L, 100 mg/L and 200 mg/L, the porcine myoglobin titers were 218.96, 242.92 and 204.45 mg/L respectively. The corresponding fermentation strain was *P. pastoris* X33-α GAP-Mb.

(2) Production of porcine myoglobin by fermentation of *P. pastoris* X33-α G1-Mb

Figure 8:
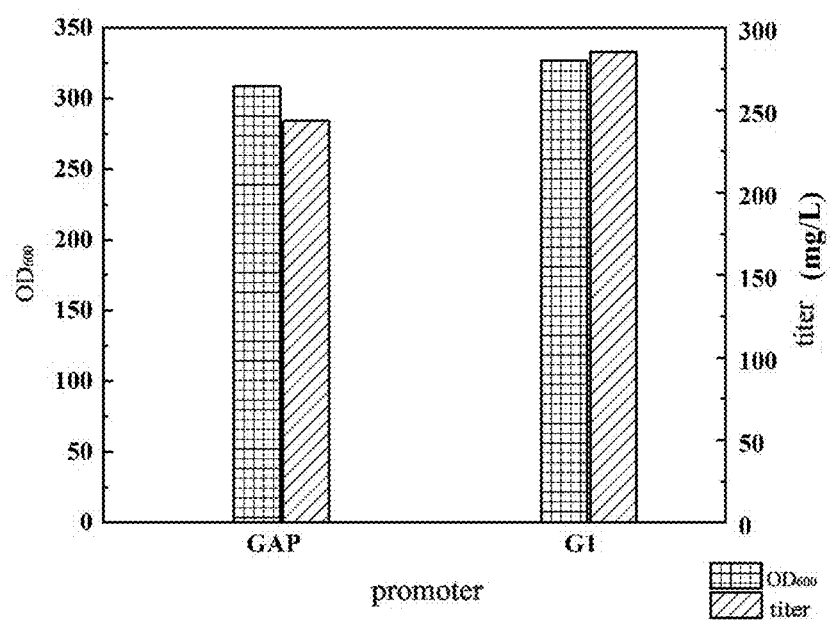
FIG. 8 shows comparison results of culture at the fermenter level of recombinant *P. pastoris* containing GAP and G1 promoters respectively.

*P. pastoris* X33-α G1-Mb was prepared into a seed solution according to the above steps and fermented, and the results are shown in FIG. 8. The detection results of the porcine myoglobin titers corresponding to the two strains *P. pastoris* X33-G1-Mb and *P. pastoris* X33-α GAP-Mb are shown in the figure. The porcine myoglobin titer corresponding to the *P. pastoris* X33-α GAP-Mb strain is 243.43 mg/L, and the porcine myoglobin titer corresponding to the *P. pastoris* X33-G1-Mb strain is 285.42 mg/L.

Figure 9:
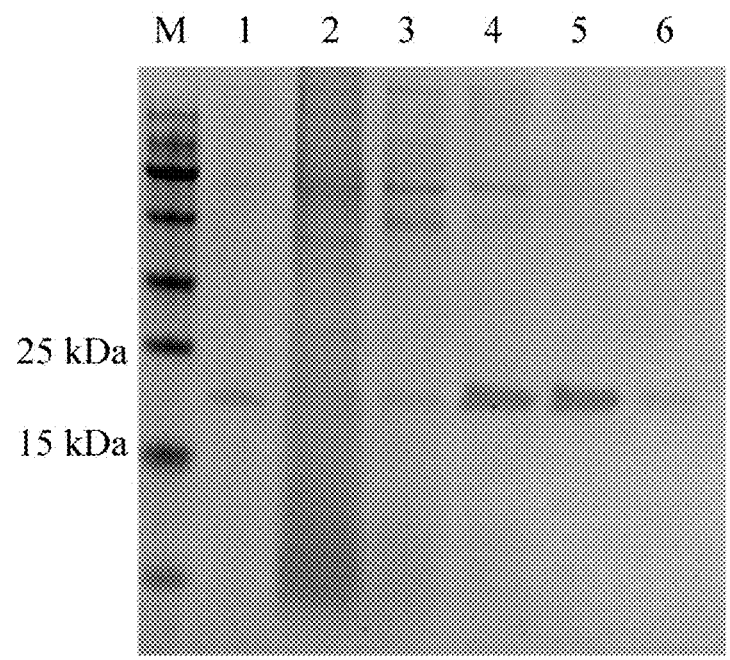
FIG. 9 shows a SDS-PAGE electrophoretogram of concentrated proteins salted out with different concentration of ammonium sulfate in Example 3.

Example 6: Separation and Purification of Porcine Myoglobin from Fermentation Broth by Salting Out-Desalting-Anion Exchange Chromatography Salting out of fermentation broth: precipitation was performed by a one-step method. Ammonium sulfate powder was slowly added to the fermentation supernatant and stirred until the concentration of ammonium sulfate reached saturations of 30%, 40%, 50%, 60%, 70% and 80%. The mixture was allowed to stand at 4° C. for 2 h, and centrifuged at 4° C. at 10000 g, for 30 min to collect the precipitate. The precipitate was redissolved with 10 mM of Tris-HCl buffer at pH 9.20 and verified and analyzed by SDS-PAGE. FIG. 9 shows the results of salting out. Lanes 1 to 6 correspond to 30% ammonium sulfate, 40% ammonium sulfate, 50% ammonium sulfate, 60% ammonium sulfate, 70% ammonium sulfate, and 80% ammonium sulfate respectively. From the figure, when the concentration of ammonium sulfate was 60%, the porcine myoglobin salted out in large quantities, and when the concentration of ammonium sulfate was 80%, the porcine myoglobin was no longer concentrated. Therefore, ammonium sulfate with the concentration of 50% and 70% was used for performing two-stage salting out.

1. Two-stage ammonium sulfate precipitation (salting out): ammonium sulfate powder was slowly added to the fermentation supernatant and stirred until the concentration of ammonium sulfate reached a saturation of 50%. The mixture was allowed to stand at 4° C. for 2 h, and centrifuged at 4° C. at 10000 g for 30 min to collect the supernatant. Ammonium sulfate powder was added to the supernatant until the concentration of ammonium sulfate reached 70%. The mixture was allowed to stand at 4° C. overnight, and centrifuged at 10000 g for 30 min to collect the precipitate. The precipitate was redissolved with 10 mM of Tris-HCl buffer at pH 2. Desalting: the solution obtained in step 1 was loaded into a desalting column Sephadex G-25, and equilibrated and eluted with 10 mM of Tris-HCl buffer at pH 9.20, and an elution peak before the conductivity changed was collected by detecting the conductivity.

3. Anion exchange chromatography: the desalted sample obtained in step 2 was loaded into an anion exchange column DEAE-Sepharose, equilibrated with 10 mM of Tris-HCl buffer at pH 9.20, and then subjected to gradient elution with 1 M of NaCl buffer, and a second elution peak was collected by detecting UV 280 nm.

Figure 10:
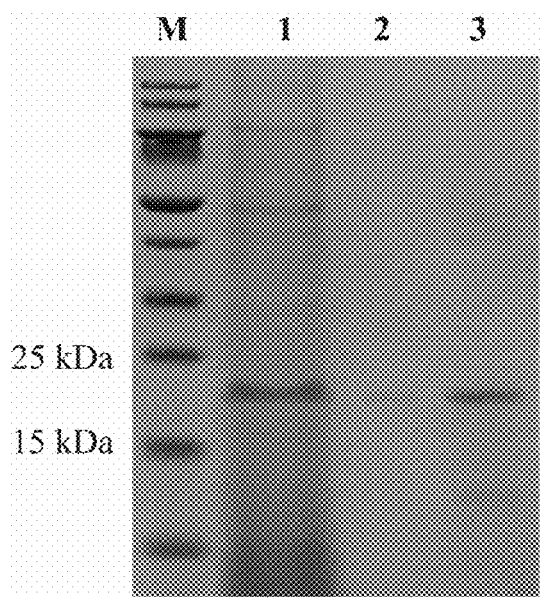
FIG. 10 shows a SDS-PAGE electrophoretogram of proteins purified by desalting-gel filtration chromatography and desalting-DEAE anion exchange chromatography.
Figure 11:
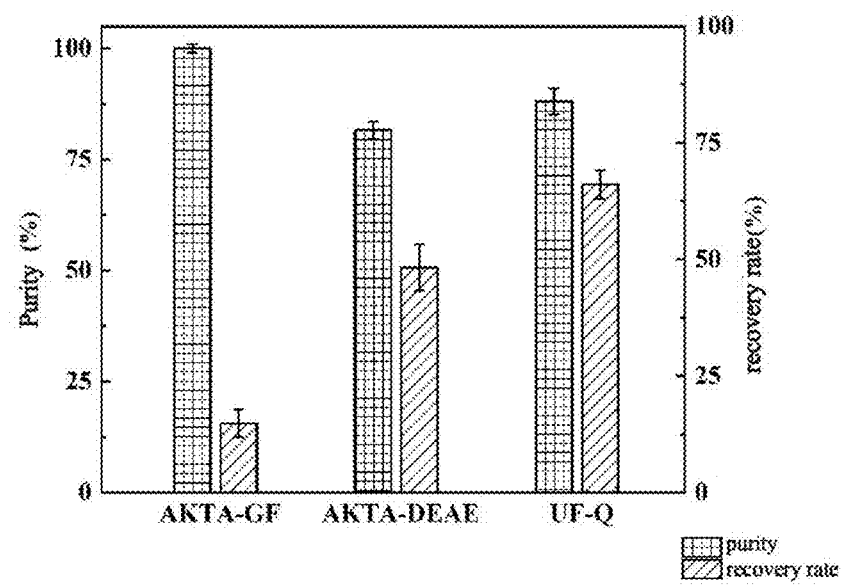
FIG. 11 shows a comparison diagram of purification rates of porcine myoglobin purified by different methods.

The samples obtained in step 2 and step 3 were verified and analyzed by SDS-PAGE respectively. The results are shown in FIG. 10. Lane 1 represents the desalting result; and lane 3 represents the purification result, the purity is 81.60%, and the purification recovery rate is 48.25%.

Example 7: Separation and Purification of Porcine Myoglobin from Fermentation Broth by Salting Out-Desalting-Gel Filtration Chromatography 1. Two-stage ammonium sulfate precipitation: same as the ammonium sulfate precipitation step in Example 3.

2. Desalting: the solution obtained in step 1 was loaded into a desalting column, and equilibrated and eluted with 10 mM of Tris-HCl buffer at pH 9.20, and an elution peak before the conductivity changed was collected by detecting the conductivity.

3. Gel filtration chromatography: the desalted sample obtained in step 2 was loaded into a Superdex gel filtration chromatographic column, equilibrated with 10 mM of Tris-HCl buffer at pH 9.20, and then eluted with 10 mM of Tris-HCl buffer at pH 9.20, and an elution peak was collected by detecting UV 280 nm.

The sample obtained in step 3 was verified and analyzed by SDS-PAGE. The result is shown by lane 2 in FIG. 10. The purity is 100%, and the purification recovery rate is 14.84%.

Example 8: Separation and Purification of Porcine Myoglobin from Fermentation Broth by Concentration-Anion Exchange Chromatography 1. Sample preparation: the concentrated fermentation broth (according to the two-stage ammonium sulfate precipitation step described in Example 6) was adjusted with Tris base to the pH of 9.20, and filtered with a 0.45 µm membrane. After that, the fermentation broth was transferred into a Vivaflow 200 membrane module return-flow system, and the myoglobin with the molecular weight greater than 10 kDa was cut off to perform concentration. The specific operation steps of the membrane module return-flow are as follows: the Vivaflow 200 membrane module was connected according to the instructions to form a return-flow system. Then, ultrafiltration concentration was performed under the action of a peristaltic pump to obtain an ultrafiltration concentrated solution.

2. Equilibration of Q anion exchange column packing material: column equilibration of Q Beads 6FF anion packing material was carried out with a buffer A solution which was 5 times the column volume.

3. Sample loading: a sample 1 time of the column volume was added and flowed down spontaneously because of gravity. After the liquid run out, the buffer A solution was added to equilibrate the sample.

4. Elution: the sample was subjected to gradient elution with buffer B solutions of different concentration (10% buffer B, and 30%-90% buffer B respectively), and the eluate was collected.

Figure 12A:
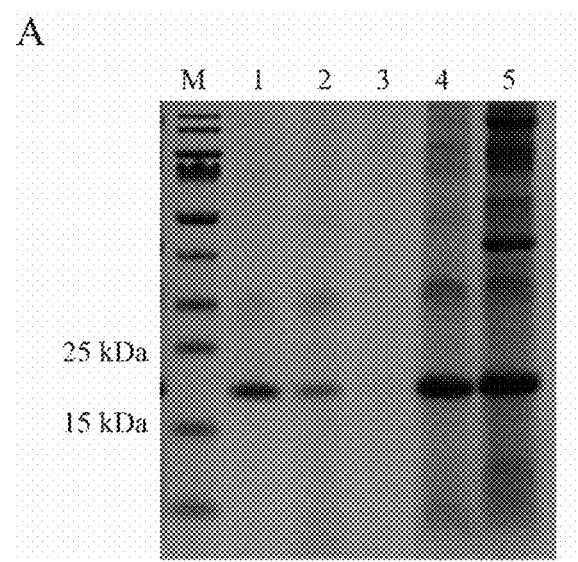
FIG. 12A shows a comparison diagram of purity of porcine myoglobin purified by different methods, and lanes 1 to 5 represent ultrafiltration concentration-Q anion exchange chromatography, desalting-DEAE anion exchange chromatography, desalting-gel filtration chromatography, ultrafiltration concentration solution 1, and ultrafiltration concentration solution 2 respectively.
Figure 12B:
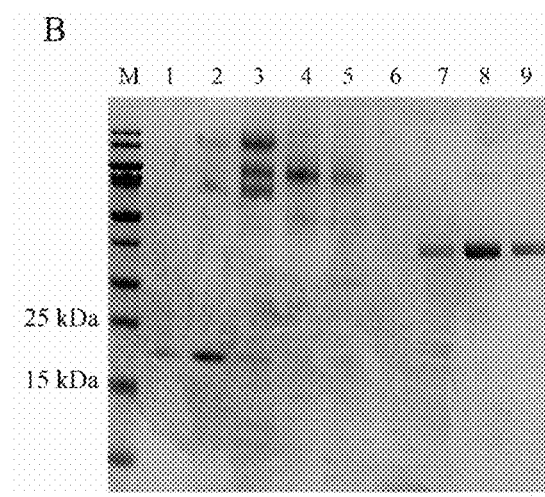
FIG. 12B shows a SDS-PAGE of protein purified by ultrafiltration concentration-Q anion exchange chromatography, and lanes 1 to 9 represent 10%, 20%, 30%, 40%, 50%, 60%, 70%, 80% and 90% concentration of NaCl respectively.

The eluates were verified and analyzed by SDS-PAGE, and the results are shown in FIG. 12. Lane 1 of FIG. 12A corresponds to the purification result, the purity is 88.04%, and the highest purification rate can reach 66.05%. FIG. 12B corresponds to gradient elution. Lane 2 corresponds to the eluate of the 20% buffer B, and lane 1 and lanes 3 to 9 correspond to the eluates of the 10% buffer B (10% salt concentration) and the 30%-90% buffer B, respectively.

Example 9: Heme Extraction and Optical Detection

1. Acidified acetone method: purified porcine myoglobin was extracted with an acidified acetone solution ($V_{acetone}$:$V_{hydrochloric\ acid}$=3:100) for 40 min, and then the pH of the solution was adjusted to neutrality using 1 M of NaOH. The resulting solution was centrifuged at 3000 g for 5 min to obtain the supernatant, and acetone was removed using a rotary evaporator. The pH of the resulting solution was adjusted to 5-7 with 1 M of HCl, and heme precipitate occurred. The solution with the heme precipitate was centrifuged at 3000 g for 15 min and washed twice with distilled water.

Figure 13:
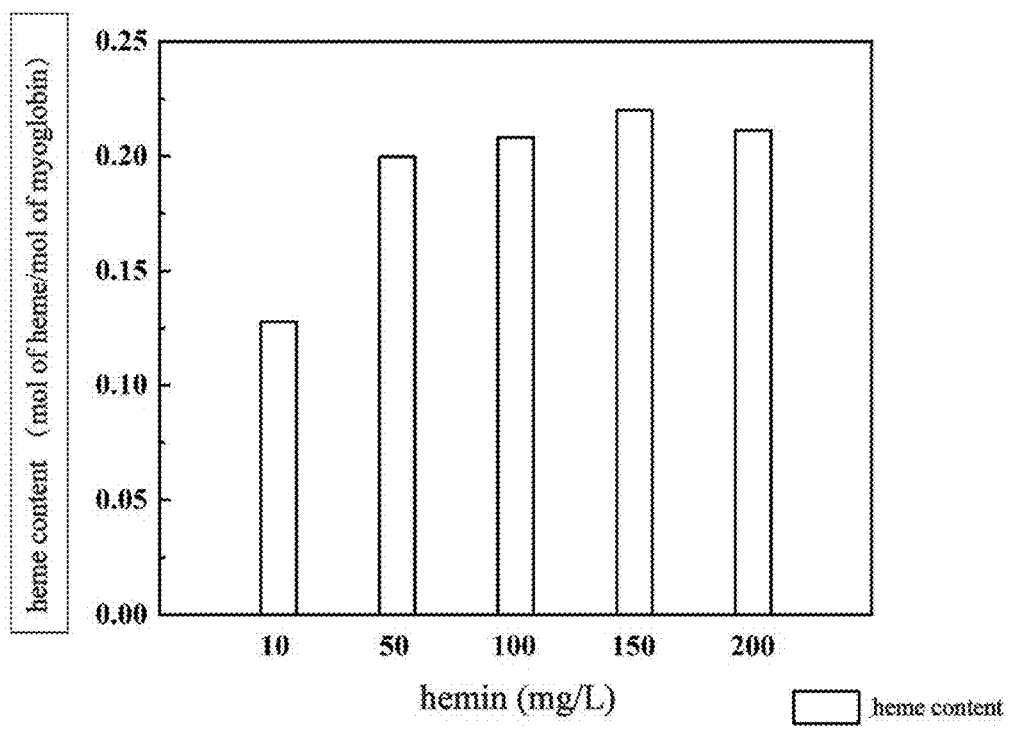
FIG. 13 is a diagram showing extraction and analysis of heme tracked in porcine myoglobin.

2. Heme extracted by the above method was detected by an optical detection method. By full wavelength scanning (200 µl of purified solutions were added to 96-well plates respectively, and then scanned at a wavelength of 200-800 nm), and characteristic peaks were determined. Then, corresponding response values were measured under the characteristic peaks, and the detection results are shown in FIG. 13.

The results show that when the concentration of exogenous substrate hemin was 150 mg/L, the amount of heme bound to the myoglobin was the highest, which was 0.22 mol of heme/mol of porcine myoglobin.

Although the disclosure has been disclosed as above in preferred examples, it is not intended to limit the disclosure. Any person skilled in the art can make various changes and modifications without departing from the spirit and scope of the disclosure. Therefore, the protection scope of the disclosure should be defined by the claims.

What is claimed is:

1. A genetically engineered P. pastoris strain comprising an expression vector, wherein the expression vector comprises a nucleotide sequence encoding an amino acid sequence of porcine myoglobin which is set forth in SEQ ID NO:13;
wherein the nucleotide sequence is SEQ ID NO:1;
wherein the expression vector comprises a glyceraldehyde-3-phosphate dehydrogenase (GAP) promoter or a G1 promoter,
wherein the nucleotide sequence encoding the G1 promoter is set forth in SEQ ID NO: 12; and
wherein the expression vector comprises a signal peptide nucleotide sequence selected from the group consisting of:
an α-factor signal peptide nucleotide sequence set forth in SEQ ID NO:44,
an α-amylase signal peptide nucleotide sequence set forth as SEQ ID NO:2,
a glucoamylase signal peptide nucleotide sequence set forth as SEQ ID NO:3,
an inulinase signal peptide nucleotide sequence set forth as SEQ ID NO:4,
an invertase signal peptide nucleotide sequence set forth as SEQ ID NO:5,
a lysozyme signal peptide nucleotide sequence set forth as SEQ ID NO:6,
a killer protein signal peptide nucleotide sequence set forth as SEQ ID NO:7,
a serum albumin signal peptide nucleotide sequence set forth as SEQ ID NO:8,
an sp23 signal peptide nucleotide sequence set forth as SEQ ID NO:9,
an nsB signal peptide nucleotide sequence set forth as SEQ ID NO: 10, and
a pre-Ost1-alpha factor signal peptide nucleotide sequence set forth as SEQ ID NO:11.

2. The genetically engineered strain according to claim 1, wherein the P. pastoris is P. pastoris X33 or P. pastoris KM71.

3. A method of producing porcine myoglobin which comprises fermenting the genetically engineered strain of P. pastoris according to claim 1 under conditions conducive to expressing the porcine myoglobin gene.

4. The method according to claim 3, further comprising inoculating the genetically engineered strain of P. pastoris into a shake flask or a fermenter comprising fermentation medium, wherein the fermentation medium comprises YPD medium, YPG medium, or BMGY medium.

5. The method according to claim 4, further comprising growing a seed solution of the genetically engineered strain of P. pastoris prior to the inoculating step,
wherein the seed solution is inoculated into the shake flask or the fermenter, and wherein the seed culture comprises the genetically engineered strain of P. pastoris which is grown in fermentation medium to an $OD_{600}$ of 6-10,
wherein the seed solution added to the shake flask or the fermenter at an amount of 1% to 5% of the total volume, and
wherein fermenting is conducted at a temperature of 25° C. to 35° C., a pH of 4.0 to 7.0, a shake speed of 150 rpm to 300 rpm, and for a time period of at least 60 hours.

6. The method according to claim 5, wherein the fermentation medium comprises 20 mg/L to 40 mg/L hemin.

7. The method according to claim 5, wherein in the fermentation medium comprises:
a) 10 g/L to 20 g/L glycerol, 10 g/L to 20 g/L glucose, or 10 g/L to 20 g/L sorbitol, and
b) 15 g/L to 25 g/L tryptone, 15 g/L to 25 g/L corn syrup, 15 g/L to 25 g/L beef extract, 15 g/L to 25 g/L diammonium hydrogen phosphate, or 15 g/L to 25 g/L ammonium sulfate.

8. The method according to claim 4, wherein the seed solution of the genetically engineered strain of P. pastoris is cultured to an $OD_{600}$ of 8-10, and wherein the seed solution is then inoculated into the fermentation medium at an amount of 5% to 10% of the total volume, and fermenting is performed at 25° C. to 35° C., an aeration rate of 1.0 VVM to 2.0 VVM, a pH of 4.0 to 7.0, and a dissolved-oxygen (DO) level of 20% to 30%, for a time period of at least 70 hour.

9. The method according to claim 8, wherein when the DO level is not less than 30%, and wherein 50 mg/L to 150 mg/L of hemin is added to the fermentation medium.

10. The method according to claim 9, wherein the fermentation medium comprises:
10 g to 30 g tryptone,
5 g to 15 g glycerol,
5 g to 15 g yeast extract, and
$1\times10^{-4}$ g to $5\times10^{-4}$ g biotin.

* * * * *